(12) United States Patent  
Masuda

(10) Patent No.: US 7,883,165 B2  
(45) Date of Patent: *Feb. 8, 2011

(54) DROPLET INFORMATION MEASURING METHOD AND APPARATUS THEREFOR, FILM PATTERN FORMING METHOD, DEVICE MANUFACTURING METHOD, DROPLET DISCHARGE APPARATUS, ELECTRO-OPTICAL APPARATUS, AND ELECTRONIC APPARATUS

(75) Inventor: Takashi Masuda, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 284 days.

This patent is subject to a terminal disclaimer.

(21) Appl. No.: 11/490,063

(22) Filed: Jul. 21, 2006

(65) Prior Publication Data

US 2006/0256147 A1 Nov. 16, 2006

Related U.S. Application Data

(62) Division of application No. 10/885,645, filed on Jul. 8, 2004, now Pat. No. 7,438,944.

(30) Foreign Application Priority Data

| Jul. 11, 2003 | (JP) | ............................. 2003-195826 |
| Jul. 11, 2003 | (JP) | ............................. 2003-195827 |
| Jul. 11, 2003 | (JP) | ............................. 2003-195829 |

(51) Int. Cl.  
*B41J 2/05* (2006.01)

(52) U.S. Cl. ................................ 347/14; 347/5; 347/19

(58) Field of Classification Search ..................... 347/5, 347/8, 9, 19, 14, 12; 435/6; 427/8  
See application file for complete search history.

(56) References Cited

U.S. PATENT DOCUMENTS

| 5,422,664 A * | 6/1995 | Stephany ..................... 347/14 |
| 6,871,930 B2 * | 3/2005 | Umetani et al. ............... 347/19 |
| 6,998,230 B1 * | 2/2006 | Schantz et al. ................. 435/6 |
| 7,393,553 B2 * | 7/2008 | Masuda ......................... 427/8 |

FOREIGN PATENT DOCUMENTS

| JP | A-07-178924 | 7/1995 |
| JP | A-7-248250 | 9/1995 |
| JP | A-09-008436 | 1/1997 |
| JP | A-10-153967 | 6/1998 |
| JP | A-11-077990 | 3/1999 |
| JP | A-11-153582 | 6/1999 |
| JP | A-11-248927 | 9/1999 |
| JP | A-11-274671 | 10/1999 |
| JP | A-2000-108216 | 4/2000 |
| JP | A-2001-133622 | 5/2001 |
| JP | A-2001-212970 | 8/2001 |

(Continued)

*Primary Examiner*—Lam S Nguyen  
(74) *Attorney, Agent, or Firm*—Oliff & Berridge, PLC

(57) ABSTRACT

A droplet information measuring method includes a preparation step of preparing a discharge head for discharging droplets, a measurement step of depositing a plurality of the droplets in series at predetermined intervals, and measuring a drying times of the plurality of droplets, and a calculation step of repeating the measurement step while varying the intervals of the plurality of droplets, and calculating a vapor diffusion distance of the droplets based upon the measurement results.

2 Claims, 16 Drawing Sheets

FOREIGN PATENT DOCUMENTS

| | | |
|---|---|---|
| JP | A-2002-066391 | 3/2002 |
| JP | A-2002-110033 | 4/2002 |
| JP | A-2002-139370 | 5/2002 |
| JP | A-2003-80694 | 3/2003 |
| JP | A-2003-094629 | 4/2003 |
| JP | A-2003-103777 | 4/2003 |
| JP | A-2003-133691 | 5/2003 |
| JP | A-2003-133692 | 5/2003 |
| JP | A-2003-149115 | 5/2003 |
| JP | A-2003-159786 | 6/2003 |
| JP | A-2003-232712 | 8/2003 |
| JP | A-2003-305831 | 10/2003 |
| WO | WO 03/029008 A1 | 4/2003 |

\* cited by examiner

DISTANCE BETWEEN DROPLETS: (a)<(b)<(c)<(d)

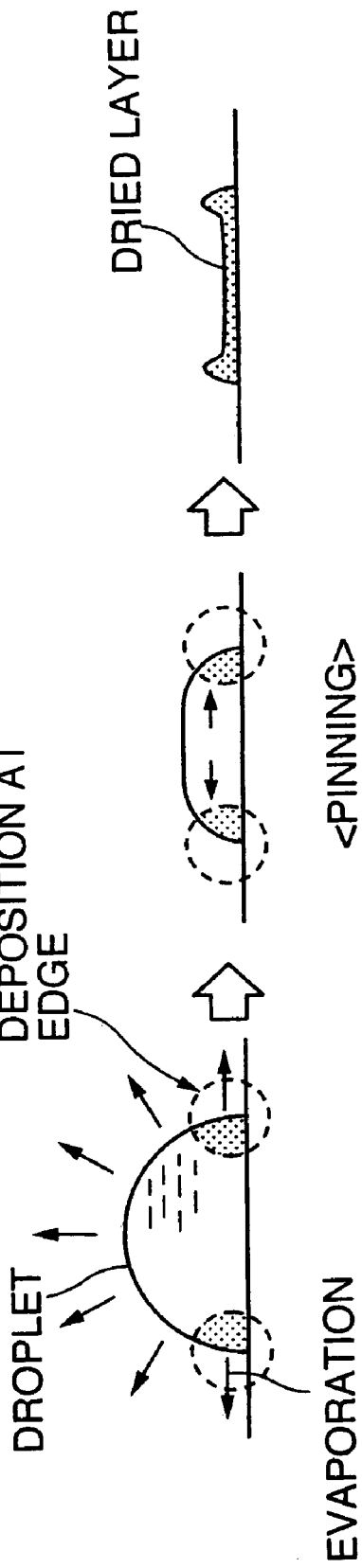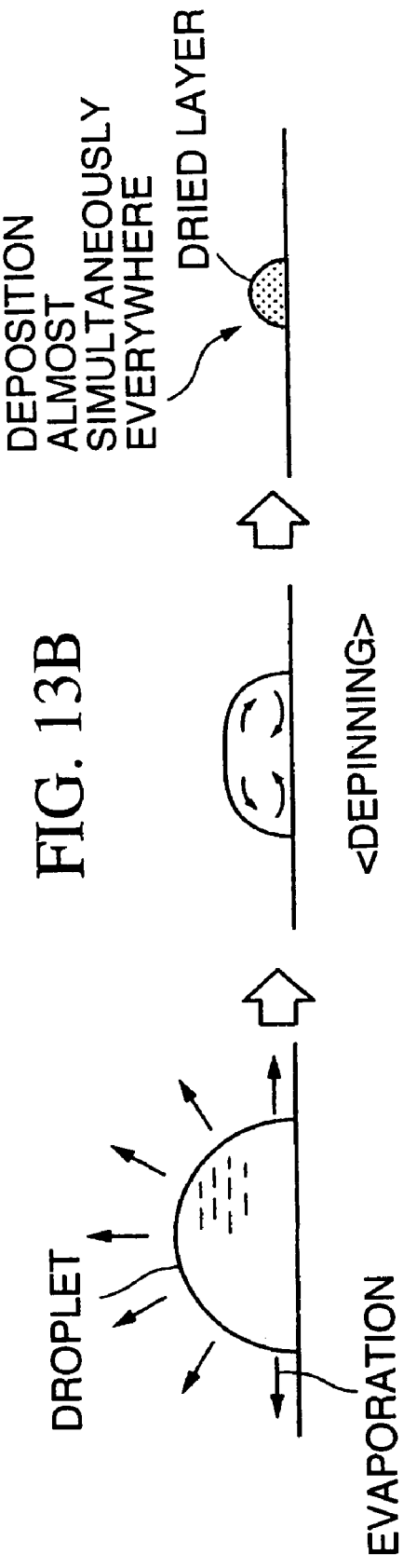

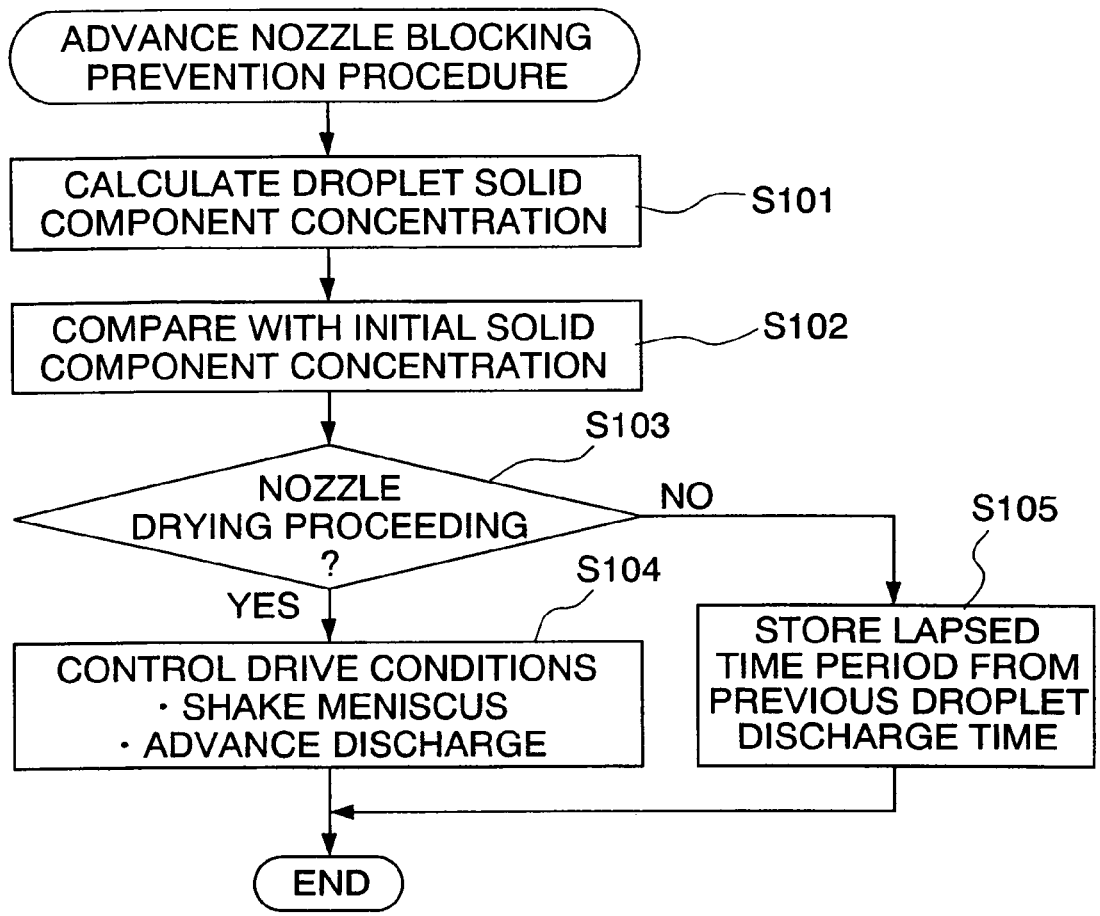
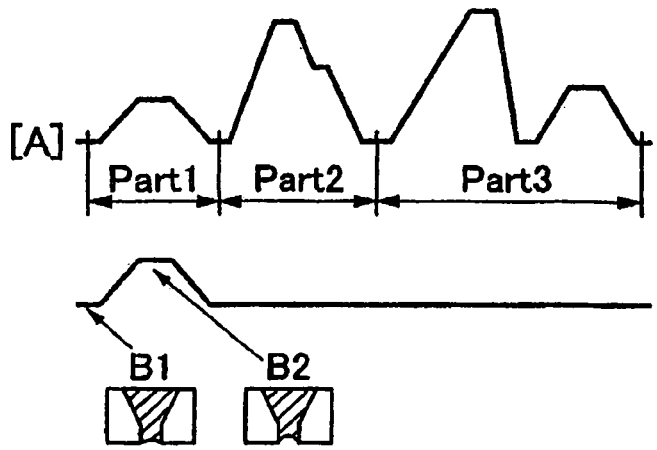

DROPLET INFORMATION MEASURING METHOD AND APPARATUS THEREFOR, FILM PATTERN FORMING METHOD, DEVICE MANUFACTURING METHOD, DROPLET DISCHARGE APPARATUS, ELECTRO-OPTICAL APPARATUS, AND ELECTRONIC APPARATUS

This is a Division of application Ser. No. 10/885,645 filed Jul. 8, 2004, now U.S. Pat. No. 7,438,944. The disclosure of the prior application is hereby incorporated by reference herein in its entirety.

BACKGROUND OF THE INVENTION

1. Field of the Invention

The present invention relates to a droplet information measuring method and a apparatus therefor, a film pattern forming method, a device manufacturing method, a droplet discharge apparatus, an electro-optical apparatus, and an electronic apparatus.

Priority is claimed on Japanese Patent Application Nos. 2003-195826, filed Jul. 11, 2003, 2003-195827, filed Jul. 11, 2003, and 2003-195829 filed Jul. 11, 2003, the contents of which are incorporated herein by reference.

2. Description of Related Art

The manufacturing process for an electronic apparatus such as an electro-optical apparatus or a semiconductor device or the like which is used as a display or a display light source or the like, includes steps of depositing a material upon a substrate, and forming a film upon this substrate. The technique for depositing material and the technique for forming a film are intimately related to the quality of the products and to their function, and are very important in the struggle for the enhancement of the performance of the above described apparatuses.

As a technique for depositing material upon a substrate, for example, as disclosed in Japanese Unexamined Patent Application, First Publication No. H11-274671, there is a method of discharging a liquid material as droplets via a nozzle which is provided to a discharge head. With this droplet discharge method, as compared to a technique such as a spin coating method or the like, there are the beneficial aspects that the waste in the consumption of the liquid material is small, and that it is easy to perform control of the amount and the position of the liquid material which is deposited upon the substrate.

In techniques for forming a film upon a substrate using a droplet discharge method, in many cases, a plurality of droplets are deposited upon the substrate in series. In such a case, it may happen that the drying conditions of a droplet may vary due to the influence of the vapor which escapes from another droplet, and this may lead to deterioration of the quality of the resultant layer.

In addition, with a droplet discharge method, it is easy for the conditions of discharge, such as the amount of discharge of the droplets from the discharge head, to vary according to the characteristics of the liquid material. Due to this, it is desirable to determine the drive conditions of the discharge head appropriately in correspondence to the liquid material which is used, such as for example the lot modification time of the liquid material and the like.

Optimization of the drive conditions, for example, may be performed by depositing a pattern of the liquid material upon the substrate, and by checking the state of this deposit. That is to say, it is performed by repeating trials of the above described pattern deposition, while varying the drive conditions of the discharge head, until the state of pattern deposition is as desired. However, this method invites a deterioration of productivity, since it requires a long time period.

In addition, for efficiently planning the optimization of the drive conditions, it is desirable directly to measure droplet information such as the mass of a droplet which has been discharged from the discharge head, and to manage the drive conditions based upon the results of this measurement. However, since the droplets which are discharged from the discharge head are very minute, a great deal of time is required for this measurement, or obtaining a stabilized measurement result may be difficult.

For example, if the amount of a droplet (its mass or its weight) is to be measured, there is a method of measuring the weight of a single droplet by measuring the weight of a large number of droplets (for example, of 5000 drops) all together, and by dividing the result of this measurement by the number of droplets; but, in this method, a lot of time and of material are required for discharging the droplets for the measurement. On the other hand, if an attempt is made directly to measure the mass of a single drop of liquid by using an accurate measuring apparatus, errors can easily arise due to the influence of the viscoelasticity of the droplet.

The present invention has been conceived in consideration of the above described circumstances, and it takes as its object to propose a method and a apparatus for measuring droplet information which can be desirably used when depositing a plurality of droplets in sequence, and in addition a droplet information apparatus which can measure information for the droplets which are discharged from a discharge head in a stable manner.

In addition, another object of the present invention is to propose a film pattern forming method, which is capable of striving for the enhancement of film quality.

In addition, another object of the present invention is to propose a device manufacturing method, an electro-optical apparatus, and an electronic apparatus, which are capable of enhancing product quality.

SUMMARY OF THE INVENTION

The first aspect of the present invention is a droplet information measuring method having a preparation step of preparing a discharge head for discharging droplets, a measurement step of depositing a plurality of the droplets in series at predetermined intervals, and measuring a drying times of the plurality of droplets, and a calculation step of repeating the measurement step while varying the intervals of the plurality of droplets, and calculating a vapor diffusion distance of the droplets based upon the measurement results.

The vapor diffusion distance which is measured by this measuring method is a quantity which indicates the diameter of the range of the influence which the vapor which escapes from one droplet exerts upon another droplet, and it is desirably utilized when depositing a plurality of droplets in series, for optimization of the deposition pitch of the droplets and the like.

In this aspect, it is possible to obtain the drying time of the plurality of droplets based upon, for example, the results of measuring the masses of the plurality of droplets during the drying process.

In this case, it is possible, for example, to deposit the plurality of droplets upon the surface of an electrode which has been provided at an upper portion of an oscillator, and to obtain the masses of the plurality of droplets based upon the results of detection of the frequency of the oscillator during the drying process of the plurality of droplets.

According to the above described method, it is possible to measure the mass and drying time, even in the case of very minute droplets.

In addition, a film pattern forming method according to the present invention include the step of depositing a liquid material as droplets upon a substrate, and wherein the vapor diffusion distance of the droplets is measured, and a deposition pitch of the droplets is determined, based upon the result of the measurement.

According to this method, it is possible to anticipate enhancement of the quality of the film produced, due to optimization of the deposition pitch of the droplets.

By, for example, determining the deposition pitch of the plurality of droplets to be long as compared with the vapor diffusion distance, the influence of vapor between adjacent droplets is avoided, so that an enhancement of the homogeneity of the film can be anticipated.

In addition by, along with determining the deposition pitch to be short as compared with the vapor diffusion distance, also depositing the next droplet after a droplet which has previously been deposited upon the substrate has dried, the influence of vapor between adjacent droplets is avoided, so that an enhancement of the homogeneity of the layer can be anticipated.

In addition, conversely, it will also be acceptable, along with determining the deposition pitch to be short as compared with the vapor diffusion distance, also to deposit the next droplet before a droplet which has previously been deposited upon the substrate has dried, and to control the drying conditions of the droplet which has previously been deposited.

In this case, for example, it is possible to keep small the drying speed of the droplet which has previously been deposited, and, as a result, it becomes possible to control the dried film of this droplet to the desired form.

Furthermore, with this film pattern forming method, the vapor diffusion distance can be measured by utilizing the above described droplet information measuring method.

In addition, in a device manufacturing method according to the present invention, the device may be created by forming a film pattern upon a substrate, and the film pattern may be formed by the film pattern forming method as described above.

According to the method, enhancement of the quality of the devices which are produced may be anticipated, since a film pattern of high quality is formed.

In addition, a droplet information measuring apparatus for measuring droplet information related to droplets discharged from a discharge head, the apparatus having an electrode which is provided so as to oppose the discharge head, an oscillator whose frequency varies corresponding to the mass of an object adhered to a surface of the electrode, a detection section which detects the frequency of the oscillator before and after the adhesion of the droplet, and a calculation section which calculates the drying time of the droplet, based upon the result of detection by the detection section.

According to the device, the above described droplet information measuring method may be implemented by the above described structure.

In this case, the calculation section may calculate the drying time, based, among the detection results of the detection section, upon the time period from the time point at which, after the discharge of the droplet, the frequency has first changed to exceed a predetermined value, until the starting time point for the frequency being in a roughly steady state continuously for longer than a predetermined time period.

In addition, when the droplet information measuring apparatus includes an impedance calculation section having a function of correcting errors due to the influence of viscoelasticity of the droplets, the calculation section may further obtain the drying speed of the droplet based upon, among the detection results of the detection section, the amount of change of frequency per unit of time within the time period.

The second aspect of the present invention is a droplet information measuring apparatus for measuring droplet information related to droplets discharged from a discharge head, the apparatus having an electrode which is provided so as to oppose the discharge head, an oscillator whose frequency varies corresponding to the mass of an object adhered to a surface of the electrode, a detection section which detects the frequency of the oscillator before and after the adhesion of the droplet, and a calculation section which calculates the mass of the solid component included within the droplet, based upon, among the detection results of the detection section, the amount of change of the frequency between before the adhesion of the droplet, and after the drying of the droplet.

According to the aspect, the mass of the solid component of the droplet is measured based upon the amount of change of the frequency of the oscillator between before the adhesion of the droplet and after the drying of the droplet. In this measurement of the mass of the solid component, any influence upon the measurement due to the viscoelasticity of the droplet is avoided, so that a stabilized measurement result is obtained.

In the above described measuring apparatus, the calculation section may further calculate the mass of the droplet which has been discharged from the discharge head, based upon the calculation results of the solid component amount of the droplet, and the solid component concentration of the liquid material. This measurement result does not include any influence of the viscoelasticity of the droplet, and has an accuracy which is stabilized.

In addition, in the above described measuring apparatus, the calculation section may calculate the time difference between the time point at which the droplet is discharged from the discharge head and the time point at which the droplet adheres to the oscillator, and calculates the speed of flying off of the droplet based upon the time difference and the distance from the discharge head to the oscillator. By doing this, it is possible to obtain a greater amount of droplet information.

In addition, a droplet discharge apparatus having, a discharge head which discharges liquid material as droplets, the above described droplet information measuring apparatus, and a control device which controls the drive conditions of the discharge head, based upon droplet information measured by the droplet information measuring apparatus.

According to the apparatus, optimization of the drive conditions of the discharge head is promoted, based upon the results of measurement by the above described droplet information measuring apparatus. Due to this, it is possible to perform a stabilized droplet discharge at high accuracy.

In the above described droplet discharge apparatus, the control device may control the drying conditions of the droplet, based upon droplet information which is measured by the droplet information measuring apparatus. By doing this, it becomes possible to control the drying conditions of the droplet.

In addition, a film pattern forming method includes the step of depositing liquid material as droplets upon a substrate, wherein the liquid material is deposited upon the substrate by the droplet discharge apparatus as described above.

According to the method, since the liquid material is deposited upon the substrate in an accurate manner, it is possible to form a film pattern at high accuracy in a stabilized manner.

In addition, in a device manufacturing method of the present invention, the device is created by forming a film pattern upon a substrate, and the film pattern is formed by the film pattern forming method as described above.

According to the method, a reduction of the cost of the device and an enhancement of product quality may be anticipated, since the film pattern is formed at high accuracy in a stabilized manner.

The third aspect of the present invention is a droplet discharge apparatus having a discharge head which discharges liquid material from a nozzle as droplets, an oscillator which varies frequency corresponding to the mass of an object adhered to a surface thereof, a detection section which detects the frequency of the oscillator before and after adhesion of the droplet, a calculation section which calculates the solid component concentration of the droplet adhered to the oscillator, based upon the results of detection by the detection section, and a control device which decides upon the drying state of the nozzle, based upon the calculation results of the calculation section.

According to the aspect, by calculating the solid component concentration of the droplet which has been discharged from the discharge head, it is possible to decide upon the state of drying of the nozzle at a stage before nozzle blocking actually occurs.

For example, by comparing together the solid component concentration of the droplet which has been discharged from the discharge head, and the initial solid component concentration of the liquid material, it is possible to decide to what extent the liquid material in the nozzle has dried.

By detecting the state of drying of the nozzle at a stage before nozzle blocking occurs, it becomes possible to prevent nozzle blocking in advance, so that it becomes possible to prevent the deterioration of the productivity which accompanies nozzle blocking.

In the above described droplet discharge apparatus, by the control device controlling the drive conditions of the discharge head, based upon the results of calculation of the calculation section, it becomes possible to prevent nozzle blocking in advance.

For example, it becomes possible to prevent nozzle blocking in advance by, at a stage before nozzle blocking actually occurs, stirring the liquid material in the nozzle via control of the drive conditions of the discharge head, and by performing the droplet discharge from the nozzle on a preliminary basis.

In addition, the above described droplet discharge apparatus may be applied to the formation of a pattern of any one of, for example, wiring, a color filter, a photoresist, a micro lens array, a electroluminescence, and a bio-material.

In addition, the electro-optical apparatus of the present invention includes a device which has been manufactured by utilizing the above described device manufacturing method.

As such a device, for example, it is possible to cite a semiconductor element, an imaging element, a liquid crystal display element, an organic electroluminescent element, or the like.

In addition, as an electro-optical apparatus, for example, it is possible to cite a liquid crystal display apparatus, an organic electroluminescent display apparatus, a plasma type display apparatus, or the like.

In addition, the electronic apparatus of the present invention includes the above described electro-optical apparatus.

According to these aspects, efforts are made to reduce the cost and to enhance the quality of the products produced.

Furthermore, the method of manufacturing an electro-optical apparatus of the present invention utilizes the above described droplet discharge apparatus.

In addition, the electro-optical apparatus of the present invention is manufactured by utilizing the above described method of manufacturing an electro-optical apparatus.

According to these inventions, efforts are made to reduce the cost and to enhance the quality of the products produced by reliably suppressing nozzle blocking during manufacture and the accompanying deterioration of product quality.

BRIEF DESCRIPTION OF THE DRAWINGS

FIG. 13A is a figure showing an example of a drying process for a droplet which corresponds to the change of frequency shown in FIG. 11, and FIG. 13B is a figure showing an example of a drying process for a droplet which corresponds to the change of frequency shown in FIG. 12.

FIG. 19 is a flow chart showing an example of processing for preventing blocking of a nozzle in advance.

FIG. 20 is a figure showing an example of a drive signal (a drive waveform) which is supplied to a piezo element.

DETAILED DESCRIPTION OF THE INVENTION

In the following, the present invention will be explained in detail with reference to the drawings.

First Embodiment

Figure 1:
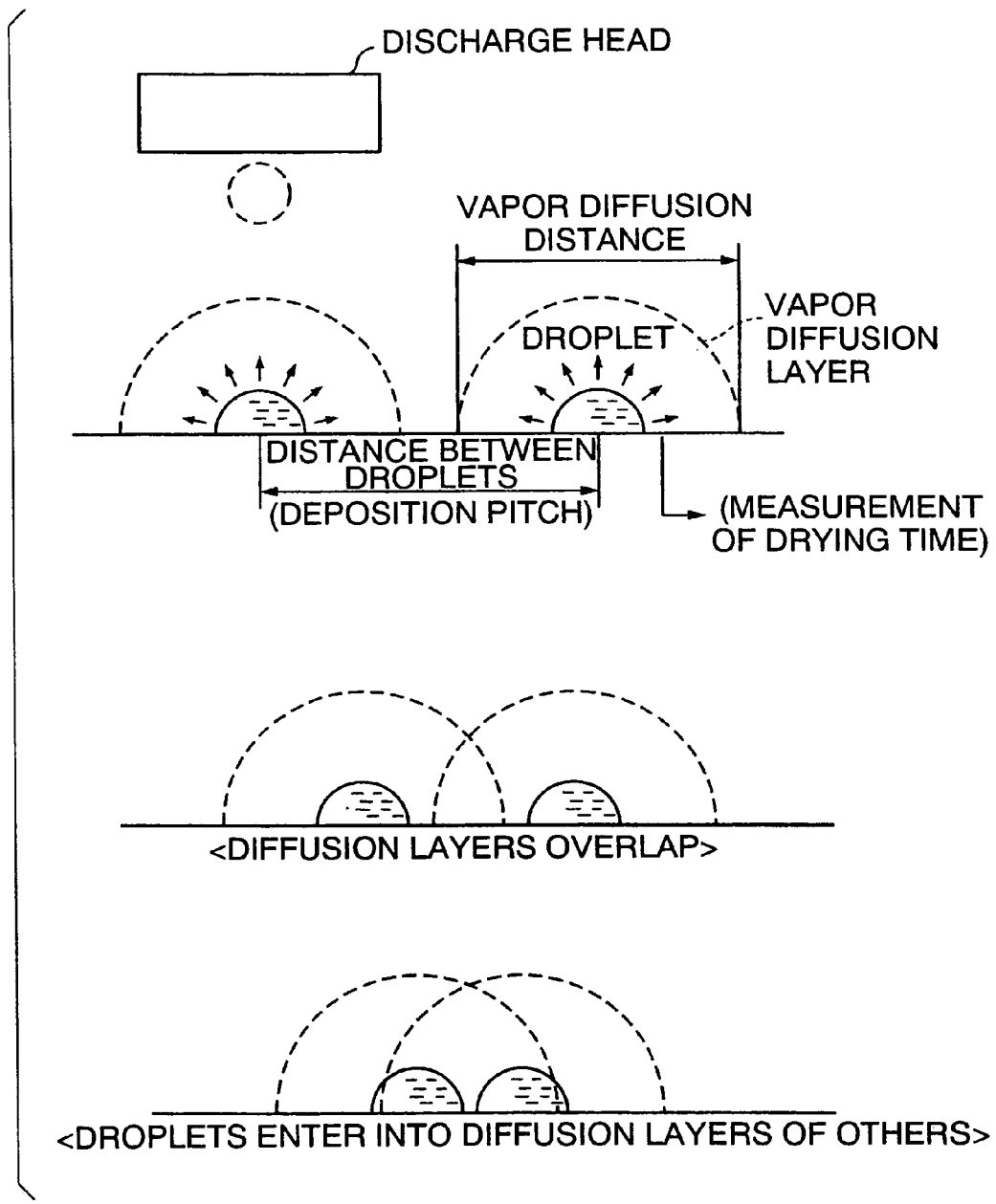
FIG. 1 is a figure showing in overall view a droplet information measuring method according to a first embodiment of the present invention.

FIG. 1 is a figure showing in overall view a droplet information measuring method according to a first embodiment of the present invention.

The droplet information measuring method of the present invention is one in which droplet information which is related to droplets of liquid material which are discharged from a discharge head are measured, and a plurality of droplets are deposited in series upon a predetermined body, and the drying times of this plurality of droplets are measured. Then a vapor diffusion distance is obtained by repeating the above described measuring step while varying the interval of the plurality of droplets (the distance between the droplets).

Here, as shown in FIG. 1, "vapor diffusion distance" is obtained as the external diameter of the vapor diffusion layer which is created around the droplets. In other words, "vapor diffusion distance" is the combined length of the diameter of the droplets and the thickness of the vapor diffusion layer, and it indicates the diameter of the vapor diffusion range. When the droplets dry, the vapor which comes off into the vapor phase from the liquid phase diffuses three dimensionally in the centers of the droplets. By the vapor diffusion layer is meant the region in which a concentration gradient is created in the vapor phase in the vicinity of the droplets, due to the movement by diffusion of molecules which have evaporated from the droplets. Here, in the broad sense of the term, "vapor diffusion layer" is taken to include a vapor layer which is created in the vapor phase in the vicinity of the droplets, and which has a concentration which experiences an influence from other droplets. In addition, the distance between the droplets is taken as being the interval between the centers of two adjacent ones of the droplets. Furthermore, the thickness of the vapor diffusion layer varies according to the nature of the liquid material, the concentration of its solid component, the temperature of the environment, and so on.

When a droplet is present within the vapor diffusion layers of another droplet, or when the vapor diffusion layers of two adjacent droplets partially mutually overlap one another, the speed of evaporation of the droplet changes, due to change of the vapor concentration at the surface of the droplet, and the like. In concrete terms, the shorter is the distance between the droplets, the greater is the distance by which their vapor diffusion layers overlap one another, and the lower does the speed of evaporation of the droplets (their drying speed) become, so that the longer does their drying time become. On the other hand, if the vapor diffusion layers do not overlap one another, the speed of evaporation of the droplets, and their drying time, almost do not alter, even if the distance between the droplets changes.

Accordingly, it is possible to obtain the vapor diffusion distance of the droplets by measuring the drying time of the droplets while varying the distance between the droplets. For example, when the distance between the droplets is gradually changed, it is possible to obtain the vapor diffusion distance from the transition distance between the droplets at which the drying time ceases to change in correspondence to change of the distance between the droplets. This transition distance between the droplets is taken as being the vapor diffusion distance. The vapor diffusion distance of the droplets which has been measured is desirably used when depositing a plurality of droplets in series, in order to optimize the deposition pitch of the droplets and so on. Furthermore, the vapor diffusion distance which is measured by this method has high utility, since it is obtained based upon an actual phenomenon.

Here, in the above described measurement method, the drying time of the droplets may be obtained by measuring the masses of the droplets during the drying process. In other words, with respect to the passage of time, the masses of the droplets change during drying, and become constant after drying. Due to this, it is possible to obtain the drying times of the droplets by obtaining the periods over which the masses of the droplet vary. In addition, the masses of the droplets can be measured accurately by using an oscillator. A measuring apparatus for the masses of the droplets which uses an oscillator, and a droplet discharge apparatus which incorporates it, will be explained below.

FIG. 2 is a figure showing an example of the structure of a droplet discharge apparatus which includes an appropriate measuring apparatus for implementing the measurement method of the present invention.

In FIG. 2, the droplet discharge apparatus 100 includes a discharge head which discharges liquid material in the form of droplets by a droplet discharge method, a stage 102, a droplet information measuring apparatus 150, and a control device 105 which controls these elements dynamically, and the like.

As a technique for discharging by a droplet discharge method, there may be suggested a static electric control method, a pressure vibration method, an electromechanical conversion method (a piezo method), an electro-thermal conversion method, an electrostatic induction method, or the like; and, in the present example, an electromechanical conversion method (a piezo method) is employed. Such a piezo method is one which takes advantage of the property that a piezo element (a piezoelectric element) deforms when it receives a pulse type electrical signal, so that a material which has been stored in a space is subjected by the deformation of the piezo element to pressure via a flexible element, whereby this material is pressed out from this space and is discharged from a nozzle. Since the droplet discharge by the piezo method does not subject the material to heat, there is the beneficial aspect that it is difficult for it to exert any influence upon the composition of the material.

The discharge head 101 includes a pressure chamber 110, a piezo element 111, and a nozzle 112. Among these, the pressure chamber 110 is connected to a tank which is not shown in the figure which stores liquid material, and periodically stores liquid material which has been supplied from the tank. In addition, the piezo element 111 deforms an inner surface of the pressure chamber 110 according to a drive signal which is supplied from the control device 105, and increases or decreases the pressure upon the liquid material within the pressure chamber 110. According to this increase and decrease of the pressure of the liquid material due to this piezo element 111, the liquid material is discharged by the discharge head 101 from the nozzle 112 as droplets. The amount of distortion of the piezo element 111 is controlled by varying the value of the electrical voltage which is applied to the piezo element 111. In addition, the speed of distortion of the piezo element 111 is controlled by varying the frequency of this applied electrical voltage. By controlling the drive conditions (the waveform of the drive signal) for the piezo element 111, it is possible to control the discharge conditions for the droplets by the discharge head 101, such as the amount of material in a single droplet (its mass), the speed at which the droplets are projected, the straightness of projection of the droplets, and so on. In addition, the discharge head 101 is supported by a head carriage 108 so as to be freely shiftable in a predetermined direction. This head carriage 108 comprises a drive device which is not shown in the drawings, and, based upon commands from the control device 105, the position of the discharge head 101 is set to a predetermined position.

The stage 102 supports a substrate P for patterning, which is taken as being the object body upon which the liquid material is to be deposited, and it comprises a drive device not shown in the figures, and, based upon commands from the control device 105, it shifts the substrate P in a predetermined direction. It is possible to deposit the liquid material in a pattern upon the substrate P by repeatedly depositing droplets upon the substrate P while shifting the discharge head 101 and the substrate P relative to one another. In addition, it is possible to create a linear pattern upon the substrate P by depositing the plurality of droplets sequentially in series upon the substrate P when performing the above described relative shifting.

The measuring apparatus 150 is a device which measures droplet information such as the mass and the like of the droplets which are discharged from the discharge head 101 by taking advantage of the characteristics of a piezoelectric element (in this example, a quartz crystal oscillator 124), and it comprises a pulse generation section 120, a sensor tip 121, a frequency counter 122 which serves as a detection section, an impedance calculation section 130, and a calculation section 131 and the like. The pulse generation section 120 is a device which supplies a pulse signal to the sensor tip 121, and which thereby causes the quartz crystal oscillator 124 to vibrate. The measurement of the droplet information is performed in order, for example, to check that the droplets are being discharged in a desired state; and, for example, it is performed before depositing the liquid material from the discharge head 101 upon the substrate P, or while depositing the liquid material.

Figure 3:
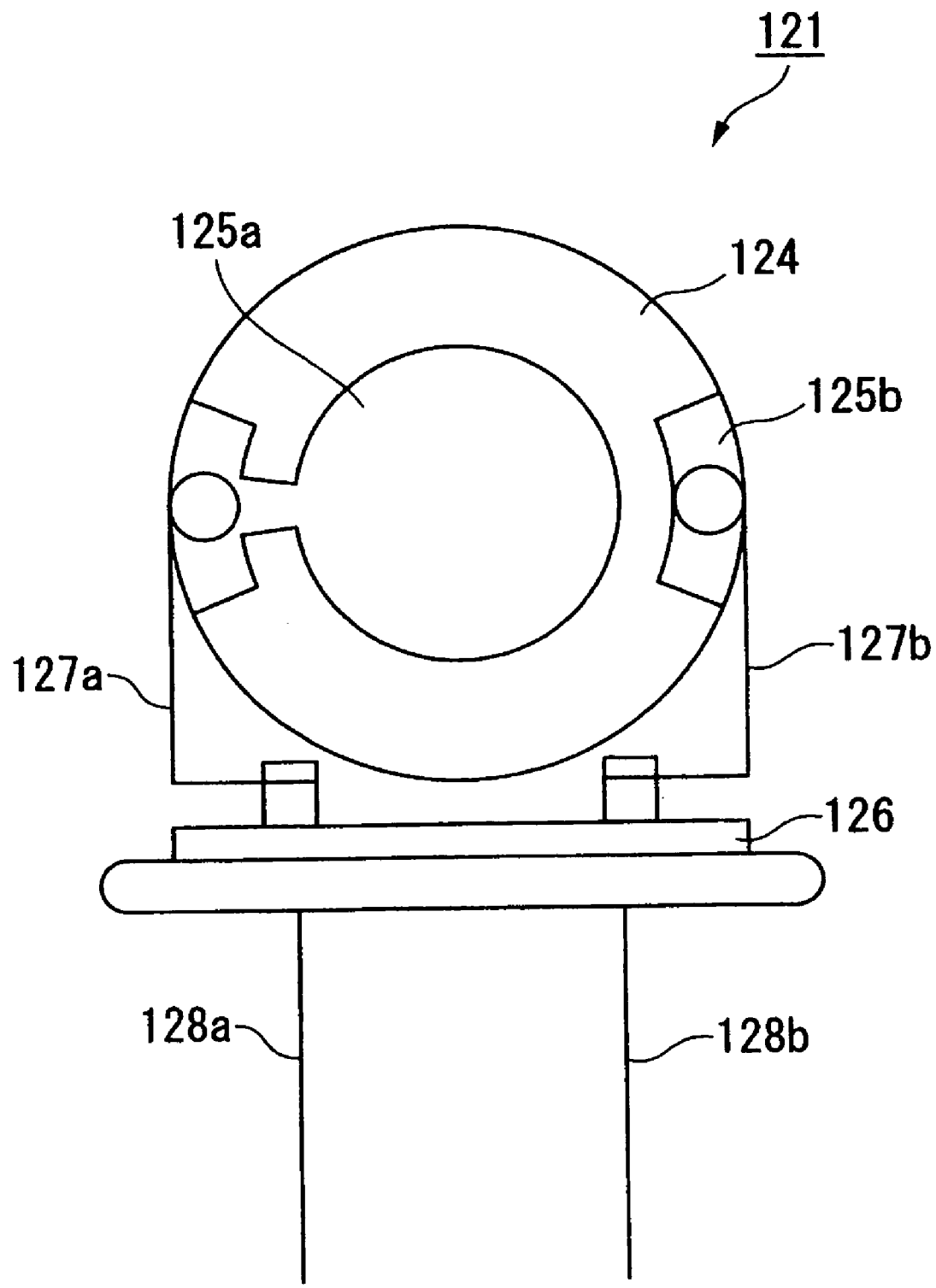
FIG. 3 is a figure showing the structure of a sensor tip.

FIG. 3 is a figure showing the structure of the sensor tip 121.

Referring to FIG. 3, the quartz crystal oscillator 124 is a piezoelectric element such as, for example, an "AT cut quartz crystal" oscillator or the like, and a pair of electrodes 125*a* and 125*b* are fixed to two surfaces thereof so as approximately to oppose one another. In addition, via supports 127*a* and 127*b* which are endowed with electrical conductivity, an insulating body 126 supports the quartz crystal oscillator 124 so that it is free to vibrate. The support 127*a*, along with leading to the electrode 125*a*, is also connected with a terminal 128*a* which is fixed to the insulating body 126. On the other hand, the support 127*b*, along with leading to the electrode 125*b*, is also connected with a terminal 128*b* which is fixed to the insulating body 126. By the above described structure, the pulse signal which is outputted from the pulse generation section 120 (refer to FIG. 2) is inputted to the sensor tip 121 via the terminals 128*a* and 128*b*, and thereby the quartz crystal oscillator 124 vibrates at its resonant frequency.

Figure 4:
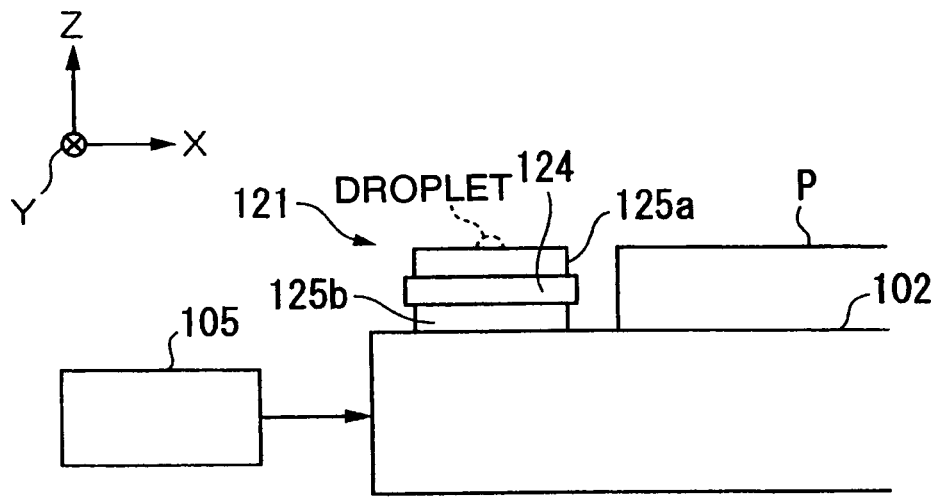
FIG. 4 is a figure showing an example of disposition of a sensor tip.

FIG. 4 is a figure showing an example of positioning of the sensor tip 121 of the measuring apparatus 104.

In FIG. 4, the sensor tip 121 is disposed upon the stage 102 which supports the substrate P. In concrete terms, the sensor tip 121 is disposed upon the surface of the stage 102 upon which the substrate P is carried at a position which is different from the position at which the substrate P is placed, and it can be shifted in the XY plane in the figure integrally with the substrate P. In addition, with the sensor tip 121, the surface of the electrode 125*a* is positioned so as to be at roughly the same height as that of the substrate P which has been placed upon the stage 102. With this exemplary arrangement, there is the beneficial aspect that the difference in the environmental conditions between the sensor tip 121 and the-substrate P is small, so that it is possible to take advantage of the measurement result using the sensor tip 121 in an effective manner during actual processing.

Returning to FIG. 2, one of the electrodes 125 which is provided to the sensor tip 121 is provided so as to oppose the droplet discharge surface in the discharge head 101. When a droplet which has been discharged from the discharge head 101 adheres to the electrode 125*a*, the mass of the droplet which has thus adhered to the electrode 125*a* is calculated by the measuring apparatus 150. Furthermore, when this measurement takes place, the head carriage 108 shifts the discharge head 101 so that the droplet adheres to the surface of the electrode 125*a*.

The quartz crystal oscillator 124 vibrates at a constant resonant frequency if the external force which acts upon it is constant, but it is endowed with the characteristic that, when an object adheres to the surface of the electrode 125*a* and the external force changes, its resonant frequency changes according to the amount of this change. In other words, the quartz crystal oscillator 124 is endowed with the characteristic that, when an object adheres to its electrode 125*a*, it vibrates at a resonant frequency which corresponds to the mass of this object. In addition, if the object which has adhered is endowed with viscoelasticity, the resonant frequency of the quartz crystal oscillator 124 varies according to the viscosity of that object. The measuring apparatus 150 of this example is endowed with a function of correcting errors due to the influence of the viscoelasticity of the object which is measured, in other words, is an external scan type device, and it is one which obtains the mass and the viscosity of the droplets. Furthermore, it is possible to obtain the electrical impedance of the quartz crystal oscillator 124 in relation to the frequency from the relationship between the electrical voltage which is applied to the quartz crystal oscillator 124 and the current therein.

This impedance changes greatly in the vicinity of the resonant frequency. The frequency when the resistance component of the impedance becomes a minimum is the resonant frequency, and this resistance component becomes the value of the resonant resistance.

The impedance calculation section 130 obtains the value of the resonant resistance of the quartz crystal oscillator 124 by calculation, and supplies a signal which indicates this resonant resistance value to the calculation section 131. In addition, the frequency counter 122 detects the resonant frequency of the quartz crystal oscillator 124, and supplies a signal which indicates the result of this detection to the calculation section 131. The calculation section 131 takes in the signal indicating the value of the resonant resistance which has been outputted from the impedance calculation section 130, and the signal which indicates the resonant frequency which has been outputted from the frequency counter 122, and, using these, calculates the viscosity and the mass of the droplet in the following manner.

Taking the value of the resonant resistance as R, when the viscosity of the droplet which has adhered to the electrode 125*a* is taken as η, then the relationship between these is given by the following Equation:

$$R = \frac{A}{K^2}(2 \times \pi \times F \times \rho_L \times \eta)^{\frac{1}{2}} \qquad \text{< Equation 1 >}$$

Here, K is an electromechanical coupling constant for the piezoelectric material or the magnetostrictive material which indicates the degree of coupling between its electrical system and its mechanical system, "A" is the basic frequency of the quartz oscillator 124, and $\rho_L$ is the density of the droplet (ink).

In addition, if the amount of change of the resonant frequency before and after the adhesion of the droplet is Δfreq, then the relationship between this amount of change Δfreq and the viscosity η is given by the following Equation:

$$\Delta freq = -F^{\frac{3}{2}} \times \left(\frac{\rho_L \times \eta}{\pi \times \rho_Q \times \mu}\right)^{\frac{1}{2}} \qquad \text{< Equation 2 >}$$

Here, ρQ is the density of the quartz crystal oscillator 124, while μ is the modulus of elasticity of the quartz crystal oscillator 124.

On the other hand, if the mass of the droplet which has adhered to the electrode 125a is taken as being Im, then the relationship between this mass Im and the amount of change Δfreq of the resonant frequency is given by the following Equation:

$$Im = \frac{-\Delta freq \times A \times \sqrt{\mu_Q \times \rho_Q}}{2 \times F \times F}$$

Here, μQ is the AT cut quartz crystal oscillator constant.

The resonant resistance value changes according to the viscosity η of the droplet (refer to equation 1), while on the other hand the amount of change Δfreq of the resonant frequency changes according to both the viscosity η of the droplet and its mass Im (refer to Equations 2 and 3). Accordingly, in the calculation section 131, first, the viscosity η of the droplet is obtained by substituting the resonant resistance value which has been supplied from the impedance calculation section 130 into Equation 1.

Next, the calculation section 131 calculates the amount of change Δfreq of the resonant frequency of the quartz crystal oscillator 124 before and after adhesion of the droplet by using the resonant frequency which is supplied from the frequency counter 122, and obtains the mass Im of the droplet by calculating Equation 2 and Equation 3, using the amount of change Δfreq and the viscosity η.

Furthermore, when the calculation section 131 obtains the viscosity η and the mass Im of the droplet, it supplies droplet information specifying these values to the control device 105.

Figure 5:
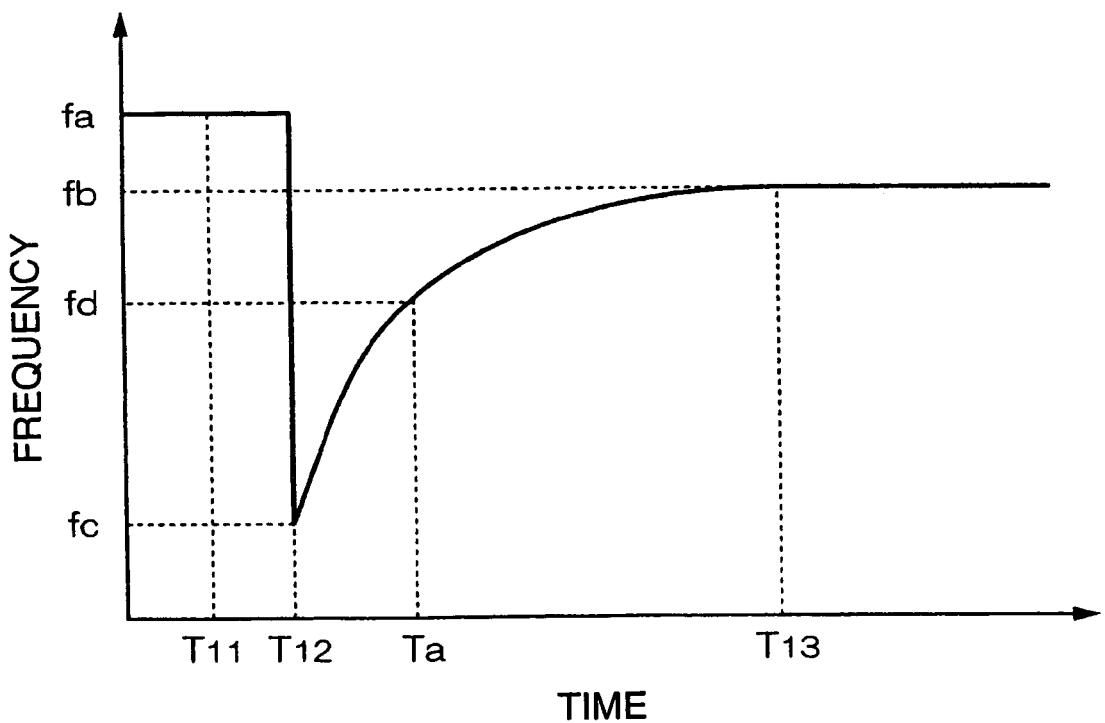
FIG. 5 is a figure showing an example of resonant frequency change of a quartz crystal oscillator.

FIG. 5 is a figure showing an example of resonant frequency change of the quartz crystal oscillator 124 of the measuring apparatus 150 of this example. The resonant frequency shown in FIG. 5 is one which takes into account the influence due to the viscoelasticity of the droplet.

In FIG. 5, the time <T11> is the time at which the droplet has been discharged from the discharge head 101, the time <T12> is the time at which the droplet has adhered to the sensor tip 121 (to its electrode 125a), and the time <T13> is the time at which the droplet has finished drying. Among these, the discharge time <T11> of the droplet is obtained from the drive signal which is supplied to the discharge head 101. In addition, it is possible to obtain the adhesion time <T12> by detecting the time point at which, after the discharge of the droplet, the frequency first has changed to exceed a predetermined value. The amount of change of the frequency which is to be the decision standard for adhesion is appropriately determined according to the intended discharge amount of material in the droplet, and according to the nature of the liquid material which is being used, and the like.

In addition, during the drying of the droplet, the frequency changes according to the change of mass of the droplet due to evaporation of its liquid component (its solvent or its dispersion medium or the like). Yet further, since, after the droplet has dried, its mass ceases to change because its liquid component has totally evaporated, accordingly the frequency attains a roughly steady state with respect to lapse of time. Accordingly, after discharge of the droplet, it is possible to obtain the time <T13> at which this droplet finishes drying, by detecting the starting time point of a roughly steady state of the frequency which continues for more than a predetermined time period. The continuation time period for the roughly steady state which is to be the standard for this detection is suitably determined according to the characteristics of the measuring apparatus 150, and according to the measurement accuracy which is required.

It is possible to calculate the mass of the droplet upon its adhesion (the discharge amount) from, among the results of frequency detection, the difference <fa−fc> between the frequency <fa> before adhesion of the droplet, and the frequency <fc> at the time of adhesion of the droplet (at the adhesion time <T12>). In other words, it is possible to obtain the mass of the droplet by substituting the above described difference in frequency <fa−fc> in the Equations as the amount of change of frequency Δfreq. In addition, in the same manner, it is possible to calculate the mass of the droplet at a predetermined time point during drying thereof from the difference <fa−fd> between the frequency <fa> before adhesion of the droplet and the frequency <fd> at the predetermined time point (for example, at the time <Ta>). This calculation is performed by the calculation section 131 (refer to FIG. 2).

Here, the time period from the adhesion time <T12> to the time of completion of drying <T13> is the time which is required for the droplet to dry (the drying time). In addition, the amount of change <fb−fc> of the frequency in this time interval <T12−T13> is in correspondence to the change of mass of the droplet during the drying process. Accordingly, it is possible to determine the average speed of drying within the drying time period, based upon the amount of change of frequency <fb−fc> per unit time period in the time period <t12−t13>. In other words, if the average drying speed is termed Va, then this is given by Va=|fb−fc|/|T12−T13|. In addition, by calculating the slope of the graph which shows the change of frequency at any given time (for example, at the time <Ta>) within the drying time period, it is possible to obtain the drying speed of the droplets at that time.

Next, the method of determining the vapor diffusion distance of the droplets by using the above described droplet discharge apparatus 100 will be explained.

Figure 6:
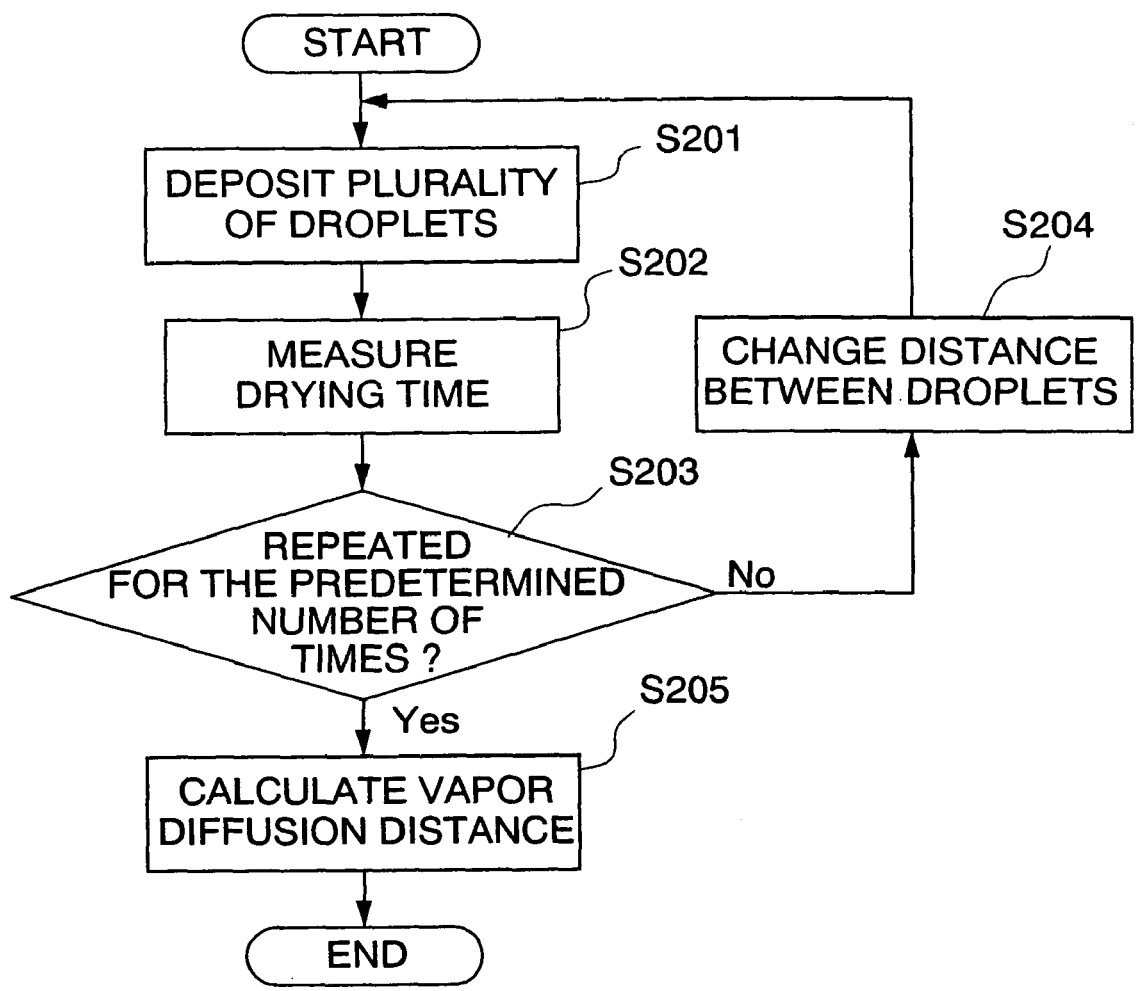
FIG. 6 is a flow chart showing an example of a procedure for obtaining the vapor diffusion distance of droplets.

FIG. 6 is a flow chart showing an example of a procedure for obtaining the vapor diffusion distance of the droplets.

First, the droplet discharge apparatus 100 discharges droplets from its discharge head 101 (refer to FIG. 2 ), and (in a step 201) deposits a plurality of droplets (in the shown example, two drops) at a predetermined interval upon the sensor tip 121 (the electrode 125a). This droplet deposition is performed by relatively shifting the discharge head 101 with respect to the sensor tip 121.

When this plurality of droplets are deposited upon the sensor tip 121, the measuring apparatus 150 measures (in a step 202) the drying time for this plurality of droplets. This measurement of the drying time is performed based upon the result of detection of the frequency of the quartz crystal oscillator 124 before and after the adhesion of the plurality of droplets, as described previously. Furthermore this measurement result is stored in a predetermined storage section in correspondence to data related to the distance between the droplets. And the above described deposition of droplets and the above described measurement of the drying time are repeated for a predetermined number of times (in steps 203 and 204), while the deposition interval of the droplets (i.e. the distance between the droplets) is varied by the droplet discharge apparatus.

Next, the measuring apparatus 150 calculates (in a step 205) the vapor diffusion distance of the droplets, based upon the measured data for the drying time of the plurality of droplets for the various distances between the droplets. Here, FIG. 7 shows, for a plurality of conditions (a) to (d) for which the distances between a plurality of droplets are different, the resonant frequency changes of the quartz crystal oscillator 124 when this plurality of droplets have been detected.

Figure 7:
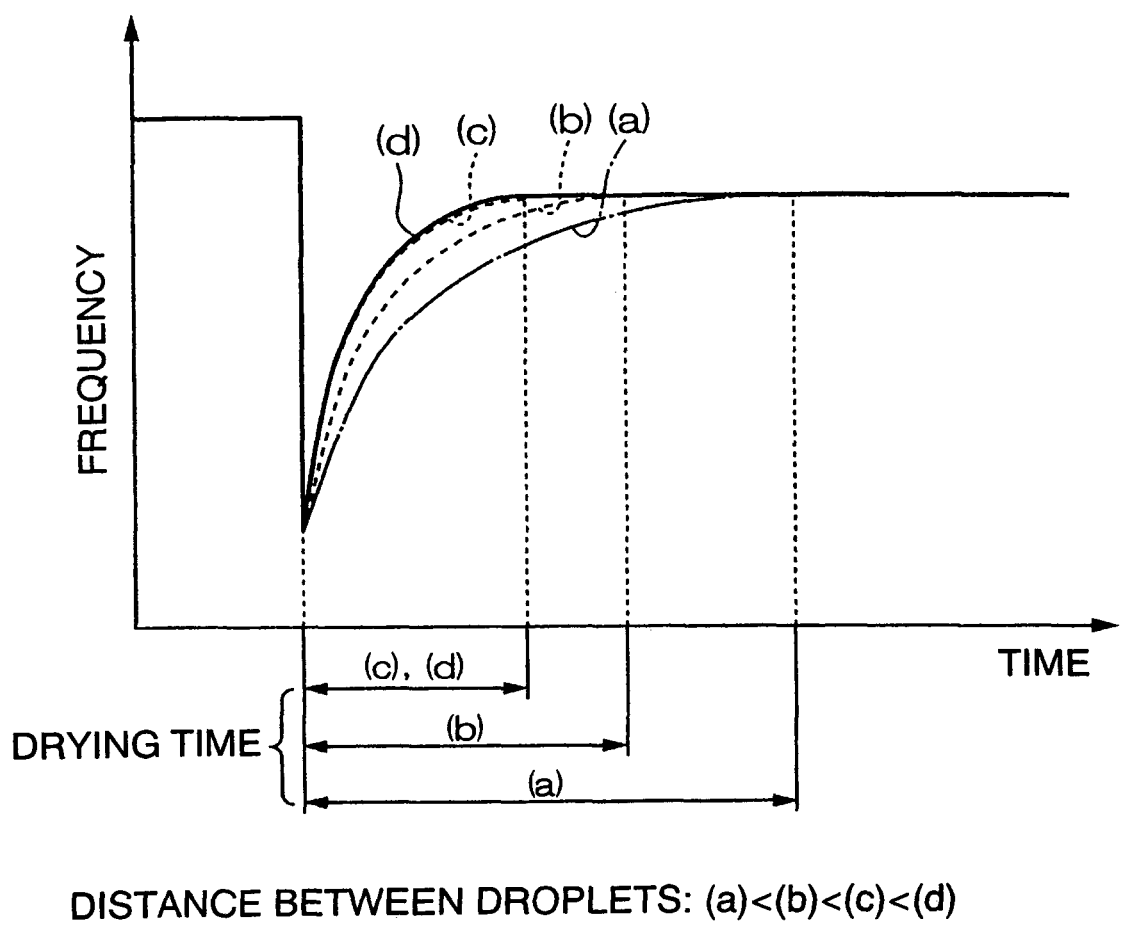
FIG. 7 is a figure showing, for a plurality of conditions (a) to (d) for which the distances between a plurality of droplets are different, the resonant frequency changes of a quartz crystal oscillator when this plurality of droplets have been detected.

As shown in FIG. 7, among the conditions (a) to (d), (a) is the one for which the distance between the droplets is the shortest, while the distance between the droplets becomes longer in order for (b), (c), and (d). The drying time for each of the conditions (a) to (d) is obtained from the behavior of the change in the resonant frequency as described previously, and it is the longest for (a), while it is the next longest for (b). In addition, the drying times for (c) and for (d) are almost the same, and are longer as compared to (b). At this time, it is possible to obtain the vapor diffusion distance from the distance between the droplets of the condition (c), which is the transition at which the drying time ceases to change with respect to change of the distance between the droplets. In other words, in this example, the distance between the droplets in the condition (c) is determined as being the vapor diffusion distance.

Furthermore, since there is a possibility that, in practice, the above described transition of change of the drying time may be between the conditions (b) and (c), it is possible to obtain a more exact vapor diffusion distance by investigating the drying time again for a distance between the droplets which is close to those conditions (b) and (c). In addition although, here, in order to determine the vapor diffusion distance, the drying times from the adhesion time of the droplets to the time of the completion of their drying are compared, this procedure is not limitative. For example, it would also be acceptable to obtain the vapor diffusion distance by comparing the times from the adhesion time of the droplets to when the amount of change of the frequency arrived at a predetermined proportion (for example, 20%).

Figure 8A:
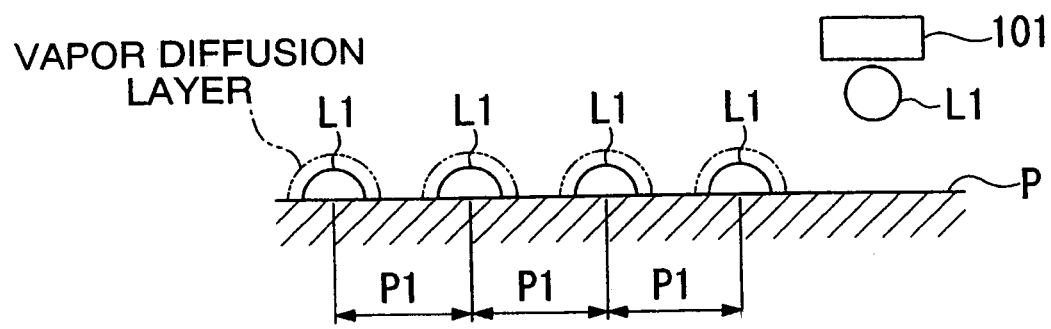
FIGS. 8A to 8C are figures showing an example of a procedure of a method for forming a linear film pattern upon a substrate.
Figure 8B:
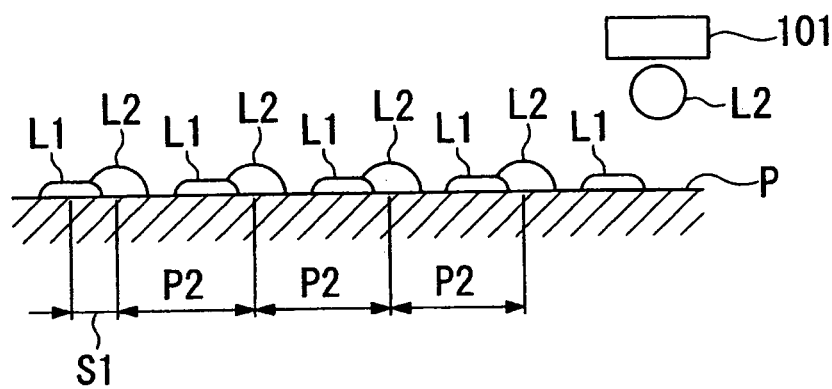
Figure 8C:
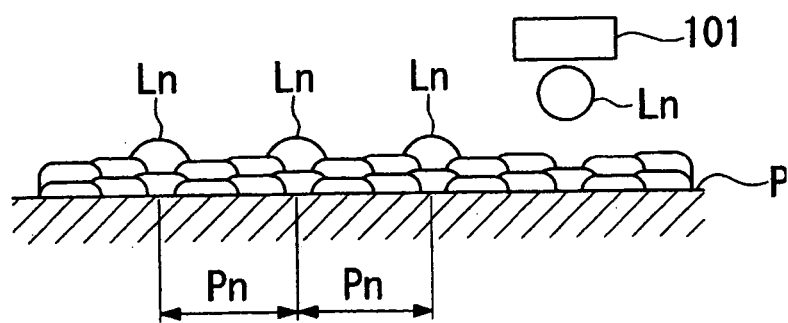

FIGS. 8A to 8C show, as one example of a film pattern forming method, an example of a procedure of a method for forming a linear film pattern upon a substrate, using the above described droplet discharge apparatus 100.

With this film pattern forming method, the liquid material is made into droplets which are discharged from the droplet discharge head 101, and these droplets are deposited upon the substrate P with a fixed distance (pitch) between them. Then, a linear film pattern is formed upon the substrate P by repeating this action of deposition of droplets.

In concrete terms, first, as shown in FIG. 8A, droplets L1 which have been discharged from the droplet discharge head 101 are deposited upon the substrate P in order with a fixed interval being allowed between them.

In this example, the deposition pitch P1 of the droplets is determined so that the vapor diffusion layers of each two adjacent droplets do not mutually overlap with one another. In other words, before depositing the liquid material from the discharge head 101 upon the substrate P, the vapor diffusion distance of droplets which are made from the same amount of the same material as the droplets which are to be deposited upon the substrate P is measured by the measuring apparatus 150. Then, the deposition pitch P1 (the distance between the droplets) is set to a distance which is longer, as compared with the vapor diffusion distance.

After having deposited the droplets L1 upon the substrate P, a drying procedure is performed, according to requirements, in order to perform elimination of the liquid component (the solvent or the dispersion medium or the like). With regard to this drying procedure, apart from employing a conventional type of heating procedure using a heating device such as, for example, a hot plate, an electric oven, a hot air blower, a lamp anneal or the like, it may be performed by shifting the stage upon which the substrate P is carried.

Next, as shown in FIG. 8B, the action of deposition of droplets described above is repeated. In other words, just as the previous time shown in FIG. 8A, liquid material is made into droplets L2 which are discharged from the discharge head 101, and these droplets L2 are deposited upon the substrate P at a fixed distance apart from one another. At this time, the amount of material in the droplets L2 (the amount of liquid material per one droplet) and the deposition pitch P2 thereof are the same as for the droplets L1 the time before. In addition, the positions of deposition of the droplets L2 are shifted by just a predetermined distance S1 from those of the droplets L1 the time before. In other words, the positional relationship between the positions of the centers of the droplets L1 the time before which have been deposited upon the substrate P and the positions of the centers of the droplets L2 this time is that they are separated by just the above described distance S1. This shift amount S1 is, in this example, narrower than the above described pitch P1, P2 (S1<P1=P2), and moreover is set so that the droplets L2 the next time partly overlap the droplets L1 which were previously deposited upon the substrate P.

In addition, at this time, although the droplet L2 this time and the droplet L1 the time before are in contact, since the liquid component is already completely or to some extent eliminated from the droplet L1 the time before, accordingly both the droplets almost do not combine together and spread out over the substrate P at all. After the droplet L2 has been deposited upon the substrate P, according to requirements, in order to eliminate the liquid component, a drying procedure is performed, in the same way as the previous time.

After this, as shown in FIG. 8C, the operation of depositing the droplets described above is repeated a plurality of times. Each time, the distance interval between the droplets Ln which are deposited (their pitch Pn) is always fixed as being the same as the distance the first time (i.e. the pitch Pn=P1). In addition, when repeating the action of depositing the droplets a plurality of times, each time, the initial position for depositing a droplet Ln is shifted by just a predetermined distance from the position at which the droplet was deposited the time before. By thus repeating the action of depositing the droplets, the gaps between the droplets which have been deposited upon the substrate P are filled in, and a continuous linear pattern is formed. In addition, the film pattern which is thus formed upon the substrate is formed by depositing the droplets always at the same pitch, and so the structure becomes homogenous, since all of it experiences almost the same formation processing.

With the film pattern formation of this example, the deposition pitches P1 and P2 of the droplets are long as compared with the vapor diffusion distance, and, since the vapor diffusion layers of neighboring droplets do not mutually overlap with one another, accordingly the influence of vapor between neighboring ones of the droplets is avoided, so that it may be expected that the homogeneity of the layer will be enhanced. In addition, even if the distance between the droplets L1 which are deposited first upon the substrate P and the droplets L2 which are deposited afterwards is short as compared with the vapor diffusion distance, by depositing the next droplets L2 after the droplets L1 which have been previously deposited have dried, it is possible to avoid any the influence of vapor between adjacent ones of the droplets. Due to this, the desired dry film is formed for each of the droplets which are deposited upon the substrate, so that it is possible to form a film pattern stably at high accuracy.

Furthermore, the method of formation of a linear pattern is not limited to the one shown in FIG. 8A to FIG. 8C. For example, it would be possible to set the deposition pitch of the droplets, or the shift amount for repetition, or the like, as desired.

Figure 9:
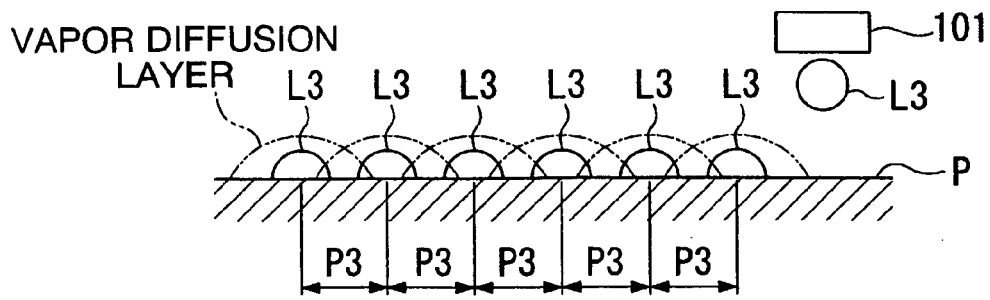
FIG. 9 is a figure showing another example of procedures of a method for forming a linear film pattern upon a substrate.

FIG. 9 is a figure showing another example of procedures of a film pattern forming method, and is a case in which the deposition pitch P3 of the droplets is determined as being short as compared with the vapor diffusion distance. In addition, before the droplets L3 which have been previously deposited upon the substrate P dry, the next droplets L3 are deposited.

With this film pattern forming method, the drying speed of the droplets is kept low, since the vapor diffusion layers of adjacent ones of the droplets mutually overlap with one another. By controlling the drying speed of the droplets in this manner, it becomes possible to control the dry film of droplets to the desired form. In particular, in this example, the evaporation at the edges of the droplets is restrained, since the drying speed is controlled by the vapor of the droplets which are deposited upon the same substrate, so that there is an advantage in controlling the shape of the dried layer.

Figure 10:
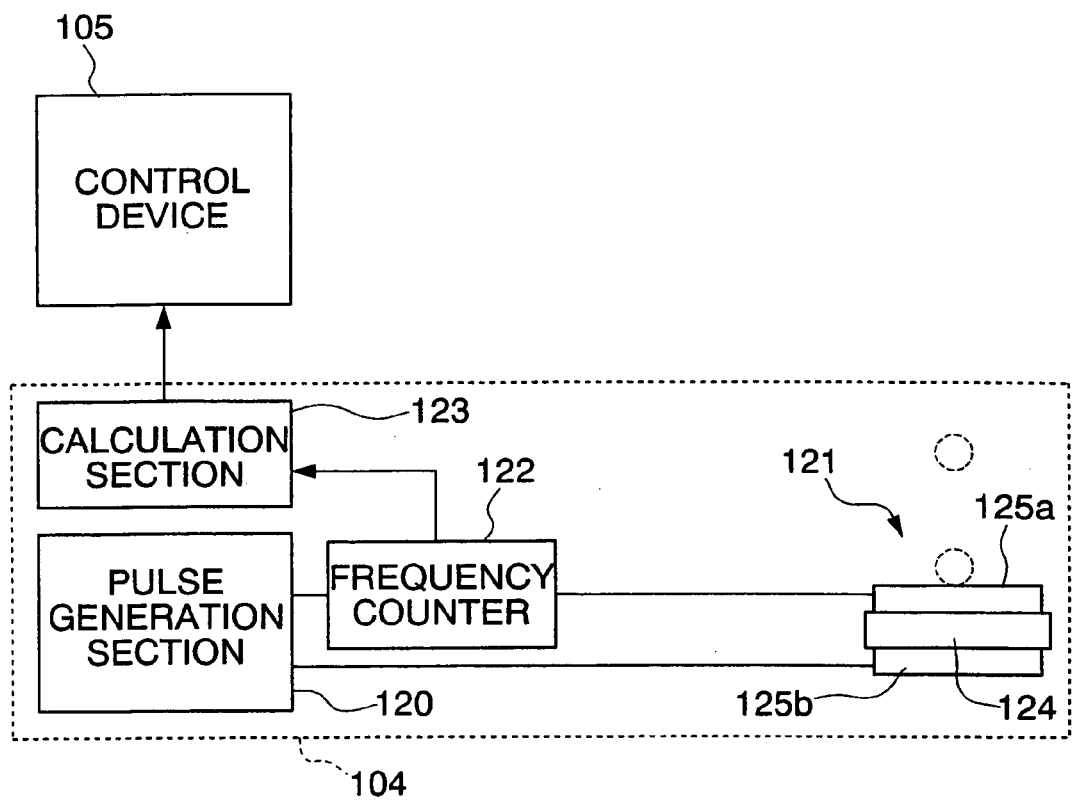
FIG. 10 is a figure showing another example of a droplet information measuring apparatus.
Figure 11:
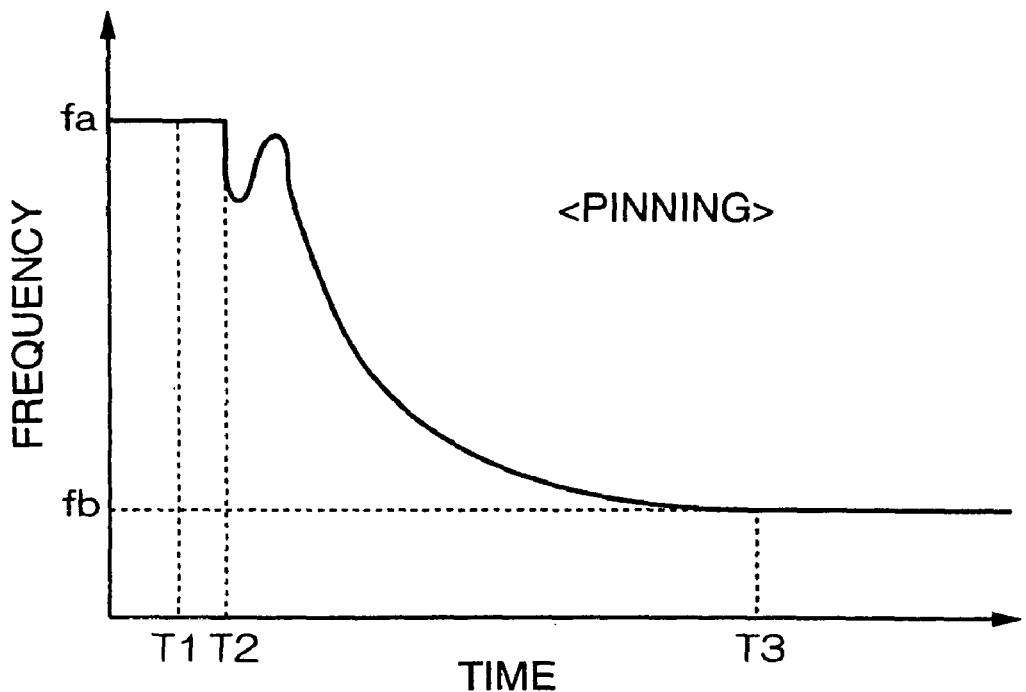
FIG. 11 is a figure showing an example of resonant frequency change of a quartz crystal oscillator in the measuring apparatus of FIG. 10.

FIG. 10 is a figure showing another example of a droplet information measuring apparatus (the measuring apparatus 104), and FIG. 11 is a figure showing an example of resonant frequency change of a quartz crystal oscillator which is detected by the measuring apparatus 104. Furthermore, with regard to the structural elements of the measuring apparatus 104, to elements which are endowed with the same function as ones in the measuring apparatus which was previously shown in FIG. 2 and FIG. 3, the same reference symbols are appended, and the explanation thereof will be omitted or simplified.

The measuring apparatus 104 shown in FIG. 10 includes a pulse generation section 120, a sensor tip 121, a frequency counter 122, a calculation section 123, and the like. The calculation section 123 inputs a signal which indicates the resonant frequency which is outputted from the frequency counter 122, and obtains the mass of the droplets by using this. The measuring apparatus 104 of this example differs from the previous measuring apparatus 150 in that it has no function of correcting the influence of viscoelasticity of the object of measurement, in other words, it is a self-excited type device. In the following, the method of calculation of the drying time by this measuring apparatus 104 will be explained.

In FIG. 11, the time <T1> is the time at which a droplet is discharged from the discharge head 101, <T2> is the time at which the droplet adheres to the sensor tip 121 (the electrode 125a), and <T3> is the time at which the droplet has finished drying. Among these, the discharge time <T1> of the droplet is obtained from the drive signal which is supplied to the discharge head 101. In addition, when the droplet adheres to the sensor tip 121, the frequency changes greatly due to the energy of the droplet when it impacts. Accordingly, it is possible to obtain the time at which the droplet has adhered to the sensor tip 121 by detecting the time point at which the frequency has initially changed after the discharge of the droplet to exceed a predetermined value. The amount of change of the frequency which is to become the decision standard is suitably determined according to the droplet discharge amount which is the target, the nature of the liquid material which is used, and so on.

In addition, with the measuring apparatus 104 of this example, due to the influence of the viscoelasticity of the droplet, while the mass of the solid component which has been deposited from the droplet is detected, the mass of the liquid component is difficult to detect. Due to this, during the drying of the droplet, the frequency changes according to the change of mass which accompanies the deposition of the solid component.

Since, after the drying of the droplet, the solid component is all solidified and there is no change of the mass, the frequency which is detected goes into a roughly steady state with lapse of time. Accordingly, after discharge of the droplet, it is possible to obtain the time <T3> that this droplet finishes drying by detecting the initial time point that the frequency continues in a roughly steady state for more than a predetermined time period. Then, the time period from the adhesion time <T1> to the time <T3> of termination of drying is the time period required for the drying of the droplet (the drying time).

Figure 12:
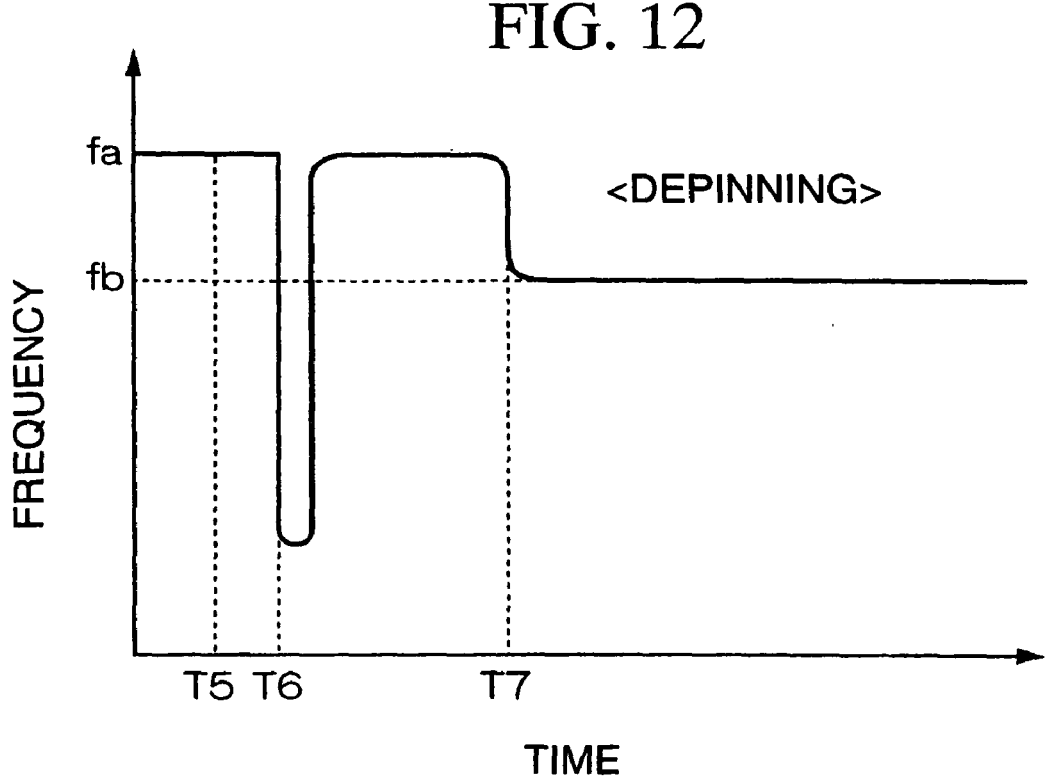
FIG. 12 is a figure showing another example of resonant frequency change of a quartz crystal oscillator.

FIG. 12 is a figure showing another example of resonant frequency change of a quartz crystal oscillator which is detected by the measuring apparatus 104. Furthermore, in FIG. 12, the drying process for the droplet which is the subject of measurement is different from the case in the previous FIG. 11.

Here, FIG. 13A is a figure showing an example of a drying process for a droplet which corresponds to the change of frequency shown in FIG. 11, and FIG. 13B is a figure showing an example of a drying process for a droplet which corresponds to the change of frequency shown in FIG. 12.

The drying process for the droplet shown in FIG. 13A is one in which the drying conditions are determined so that the solid component concentration at the edge of the droplet quickly reaches the saturation concentration, as compared with its central portion. Generally, with a droplet which has been deposited upon a body, the progress of the drying is quicker at its edge. In the drying process of a droplet, when the solid component concentration at the edge of the droplet arrives at the saturation concentration, the solid component locally solidifies at this edge. Then, due to this solid component which has solidified, the edge of the droplet comes to be in a state as though it has been pinned down, so that, as the droplet continues to dry further, its contraction (the contraction of its external diameter) is suppressed. In the following, this phenomenon, in other words the phenomenon that contraction of the droplet along with further drying is suppressed due to the solid component which has been deposited at its edge, will be termed "pinning".

On the other hand, the droplet drying process shown in FIG. 13B is one in which the drying conditions are determined so that the saturation concentration arrives at the solid component concentration all over the droplet at roughly the same time. In this case the above described pinning does not take place, since it is difficult for solidification of a local solid component to take place at the edge of the droplet, and, during the drying process, the droplet contracts along with the evaporation of its liquid component (its solvent or dispersion medium or the like). In other words, the exterior diameter of the droplet becomes smaller along with the progress of the drying. In the contraction process of the droplet, within the droplet, convection which includes a current of liquid from the central portion towards the edge and a current from the edge toward the central portion is continuously created, and accordingly it may be anticipated that, along with any local increase of the solid component concentration within the droplet being suppressed, also the solid component concentration will be made more uniform within the droplet. Then, by the solid component concentration arriving at the saturation concentration all over the droplet, deposition of the solid component takes place almost simultaneously all over the droplet. In the following this phenomenon, in other words the phenomenon of contraction of the droplet during drying without any pinning taking place, will be termed "depinning". Furthermore, the currents of liquid within the droplet which are shown by arrow signs in FIG. 13A and FIG. 13B are only exemplary, and they may be different in practice.

Returning to FIG. 12, for the frequency change which corresponds to depinning, the time <T5> is the time at which a droplet is discharged from the discharge head 101, while <T6> is the time at which this droplet has adhered to the sensor tip 121 (the electrode 125a), and <T7> is the time at which this droplet has completed drying. The discharge time <T5> of the droplet from the discharge head 101 is obtained from the drive signal which is supplied to the discharge head 101, in the same manner as described above. In addition, the adhesion time <T6> of the droplet may be obtained by detecting the time point, after discharge of the droplet, at which the frequency initially has changed to exceed a predetermined value.

In the drying process of the droplet with depinning, since almost no deposition of the solid component takes place during the period until the solid component concentration all over the droplet arrives at the saturation concentration, accordingly it is easy for the frequency which is detected to become in a roughly steady state (T6 to T7). Then, the above described solid component concentration reaches the saturation concentration at the time <T7> that the drying is completed, and the frequency greatly changes in accompaniment with the solid component being deposited over the entire extent of the droplet at the same time. After this, along with the solid component solidifying and the variation of the mass ceasing, the frequency comes to be in a roughly steady state along with the passage of time. Accordingly by detecting, after the discharge of the droplet, the initial time point that the resonant frequency continues to be in a roughly steady state for greater than a predetermined time period, it is possible to obtain this time <T7> that the droplet finishes drying. Then, the time period which is required for the droplet to dry from the adhesion time <T6> to the time <T7> that the drying is completed is the drying time. Furthermore, the time period for continuation in the roughly steady state which is taken as the standard when obtaining the drying completed time <T7> is set so that, during drying of the droplet, the frequency exceeds the time period <T6 to T7> which constitutes the roughly steady state.

Figure 14:
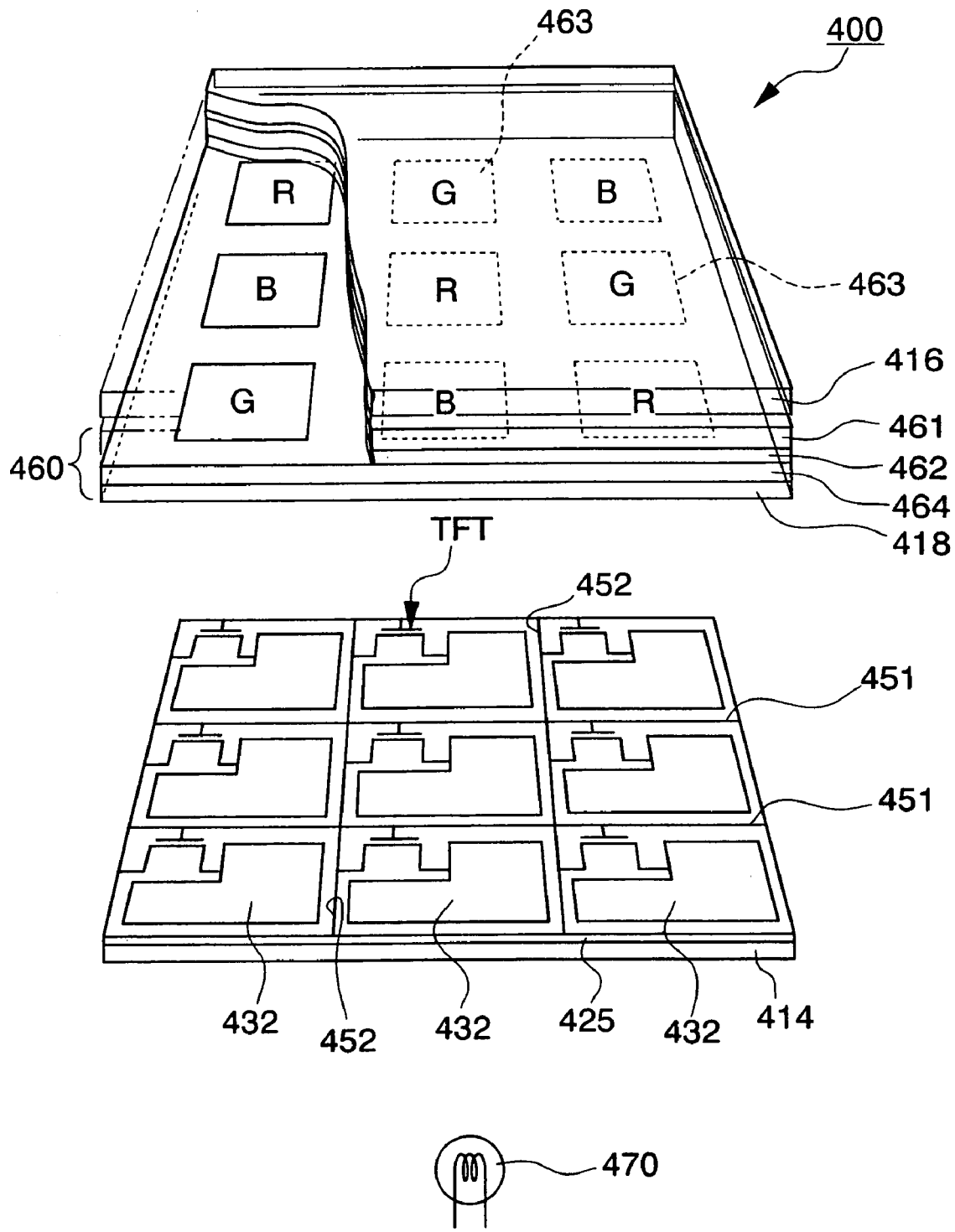
FIG. 14 is a perspective view showing an example of a structure of a liquid crystal display apparatus upon which a color filter which has been manufactured using the droplet discharge apparatus according to the present invention has been mounted.

FIG. 14 is a perspective view showing an example of a structure of a liquid crystal display apparatus upon which a color filter which has been manufactured using the droplet discharge apparatus according to the present invention has been mounted.

With the liquid crystal display apparatus according to this embodiment, peripheral elements such as a liquid crystal drive IC (not shown in the figures), lead wires or the like (not shown in the figures), a light source 470, a support (not shown in the figures), and the like are provided.

The structure of the liquid crystal display device 400 will be simply described. This liquid crystal display device 400 principally comprises a color filter 460 and a glass substrate 414 which are arranged so as mutually to oppose one another, a liquid crystal layer not shown in the figure which is sandwiched between these two elements, a light polarizing plate 416 which is attached to the upper surface side of the color filter 460 (i.e., to the side of the observer), and a light polarizing plate not shown in the figures which is attached to the lower surface side of the glass substrate 414. The color filter 460 is equipped with a substrate 461 which is made from transparent glass, and which is a substrate provided upon the side of the observer, while the glass substrate 414 is a transparent substrate which is provided to the other side thereof.

On the lower side of the substrate 461, there are formed, in order, a division wall 462 which is made from a black colored light sensitive resin layer, a colored portion 463, and a overcoat layer 464; in addition, an electrode 418 for driving is formed on the lower side of the overcoat layer 464. Furthermore, in an actual liquid crystal device, there are provided a liquid crystal layer side which covers the electrode 418, and an orientation layer over an electrode 432 which will be described hereinafter on the side of the glass substrate 414, but these will be omitted from the drawings, and from this explanation.

The electrode 418 for driving the liquid crystal which is formed upon the liquid crystal layer side of the color filter 460 is one which is made from a transparent and electrically conductive material such as ITO (Indium Tin Oxide) or the like, and which extends all over the surface of the overcoat layer 464.

An insulating layer 425 is formed over the glass substrate 414, and, over this insulating layer 425, there are formed TFTs (Thin Film Transistors) which serve as switching elements, and picture element electrodes 432.

Over the insulating layer 425 which is formed over the glass substrate 414, there are provided scanning lines 451 and signal lines 452 in a matrix form, and the picture element electrodes 432 are provided in each of the regions which are surrounded by the scanning lines 451 and the signal lines 452. The TFTs are fitted at the portions between the corner portions of each of the picture element electrodes 432 and the scanning lines 451 and the signal lines 452, and the supply of current to the picture element electrodes 432 is controlled by signals being applied through the scanning lines 451 and the signal lines 452 so as to turn these TFTs into the ON state or the OFF state.

Figure 15:
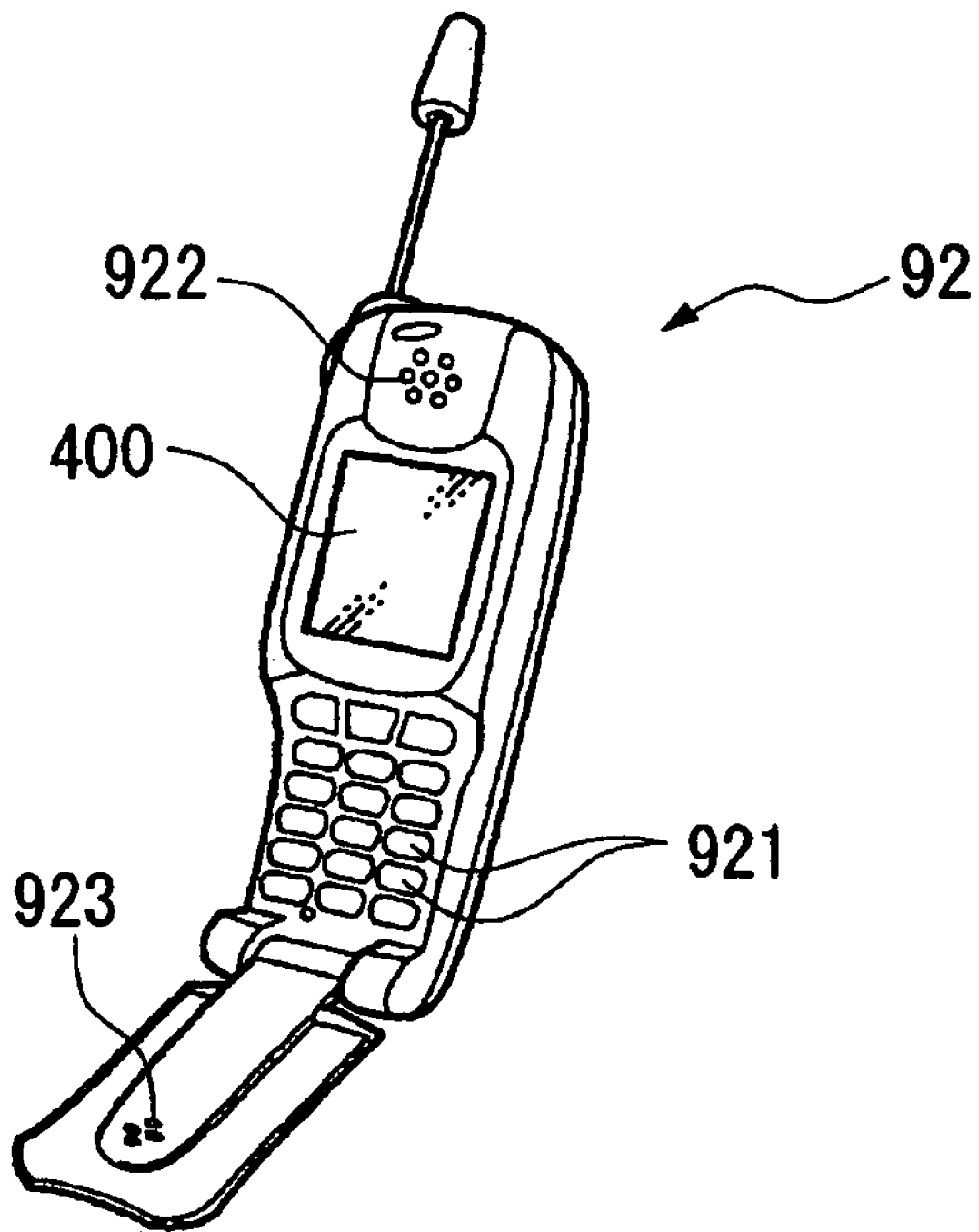
FIG. 15 is a perspective view showing an example of a structure of a portable telephone, which constitutes an example of an electronic apparatus which utilizes a liquid crystal display device.

FIG. 15 is a perspective view showing an example of a structure of a portable telephone, which constitutes an example of an electronic device which utilizes the above described liquid crystal display apparatus. In this figure, the portable telephone 92 includes the above described liquid crystal display apparatus 400, as well as a plurality of operating buttons 921 and a speech reception aperture 922 and a speech transmission aperture 923.

Second Embodiment

Figure 16:
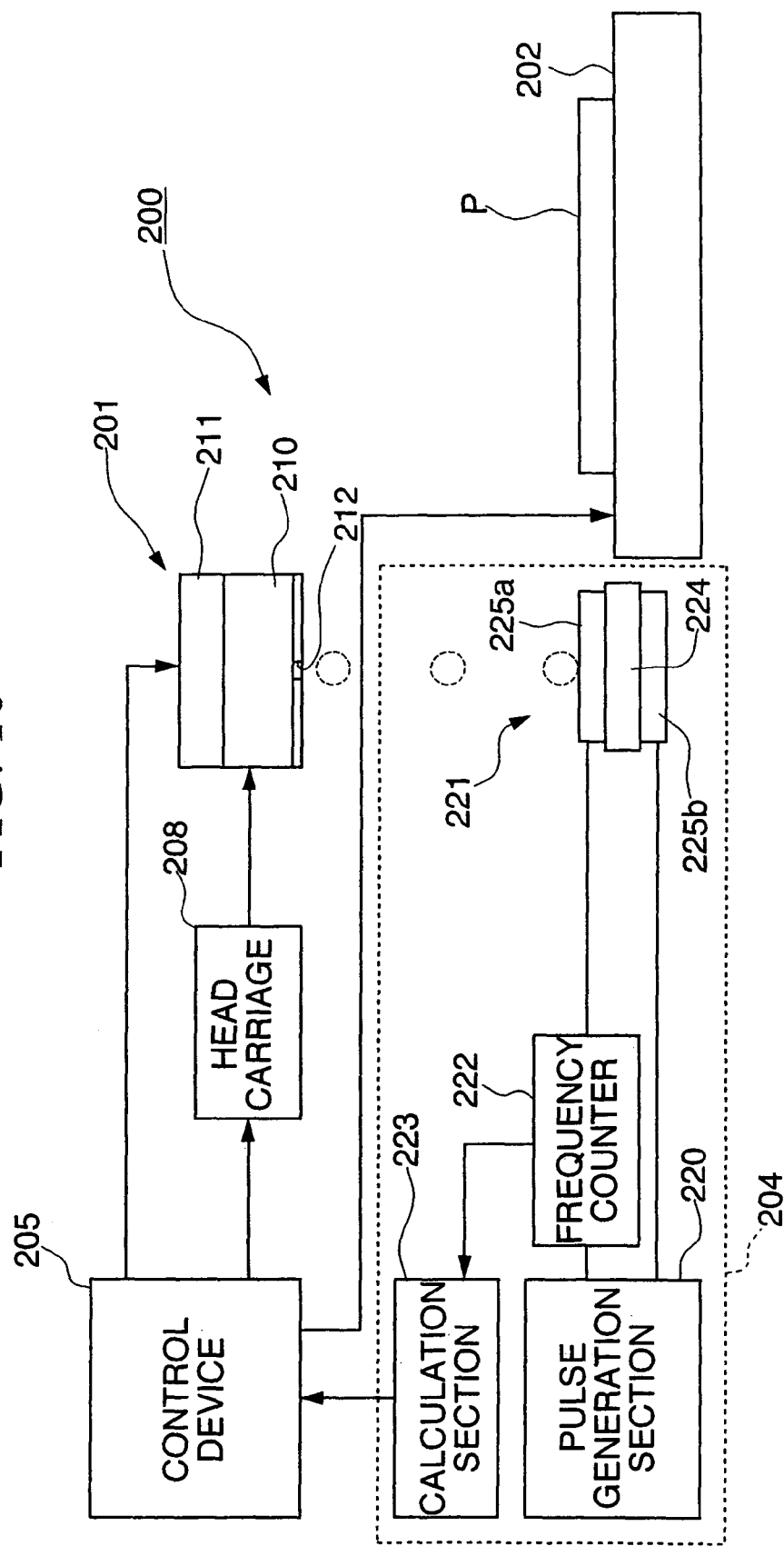
FIG. 16 is a figure showing schematically an example of the structure of a droplet discharge apparatus according to a second embodiment of the present invention.

FIG. 16 is a figure showing schematically an example of the structure of a droplet discharge apparatus according to a second embodiment of the present invention.

In FIG. 16, the droplet discharge apparatus 200 comprises a discharge head 201 which discharges liquid material in the form of droplets by a droplet discharge method, a stage 202, a droplet measuring apparatus 204, a control device 205 which controls these elements dynamically, and the like.

As the discharge technique for this droplet discharge method, there may be proposed a static electric control method, a pressurization vibration method, an electromechanical conversion method (a piezo method), an electrothermal conversion method, a static electric aspiration method, or the like; and, in the present example, an electromechanical conversion method (a piezo method) is employed. In such a piezo method, by taking advantage of the characteristic that a piezo element (a piezoelectric element) deforms when it receives a pulsed electrical signal, pressure is applied via a flexible object to a space in which a material is stored by deforming a piezo element, and the material is pressed out from this space and is discharged from a nozzle. Since such droplet discharge by a piezo method does not apply heat to the material, accordingly it is endowed with the beneficial aspect that it is difficult for it to exert any influence upon the composition of the material.

The discharge head 201 includes a pressure chamber 210, a piezo element 211, and a nozzle 212. Among these, the pressure chamber 210 is connected to a tank not shown in the figures which stores liquid material, and temporarily stores liquid material which has been supplied from the tank. In addition, the piezo element 211 causes the inner surface of the pressure chamber 210 to deform according to a drive signal which is supplied from the control device 205, and increases and decreases the pressure upon the liquid material which is within the pressure chamber 210. According to this increase and decrease of pressure of the liquid material caused by the piezo element 211, the liquid material is discharged as droplets by the discharge head 201. The amount of distortion of the piezo element 211 is controlled by varying the value of the electrical voltage which is applied to the piezo element 211. In addition, the speed of the distortion of the piezo element 211 is controlled by change of the frequency of this applied electrical voltage. It is possible to control the conditions of discharge of the droplets by the discharge head 201, such as the amount of material (the mass) per one drop of the droplets, the flying off speed of the droplets, the straightness of flying off of the droplets, and so on, by controlling the drive conditions for the piezo element (the waveform of its drive signal). In addition, the discharge head 201 is supported by a head carriage 208 so as to be freely shiftable in a predetermined direction. This head carriage 208 includes a drive device which is not shown in the figures, and sets the position of the discharge head to a predetermined position, based upon commands from the control device.

The stage 202 is an element for supporting the substrate P which is to be patterned, as an object body upon which the liquid material is to be deposited, and it includes a drive device which is not shown in the figures which, based upon commands from the control device 205, shifts the substrate P in a predetermined direction. By depositing droplets upon the substrate P repeatedly while the discharge head 201 and the substrate P are being shifted relatively to one another, it is possible to deposit the liquid material in a pattern upon the substrate P. In addition, it is possible to form a linear pattern upon the substrate P by depositing a plurality of droplets continuously upon the substrate P in series during the above described relative shifting.

The measuring apparatus 204 is a device which takes advantage of the characteristics of a piezoelectric element (in this example, the quartz crystal oscillator 224) to measure droplet information such as the mass of a droplet which has been discharged from the discharge head 201 and the like, and it includes a pulse generation section 220, a sensor tip 221, a frequency counter 222 which serves as a detection section, a calculation section 223, and the like. The pulse generation section 220 is a device which supplies a pulse signal to the sensor tip 221 and thereby causes the quartz crystal oscillator 224 to vibrate. Measurement of the droplet information is performed in order, for example, to check that the droplet is being discharged in a desired state, and it is performed, for example, before depositing the liquid material from the discharge head 201 upon the substrate p, or during the deposition of the liquid material.

Figure 2:
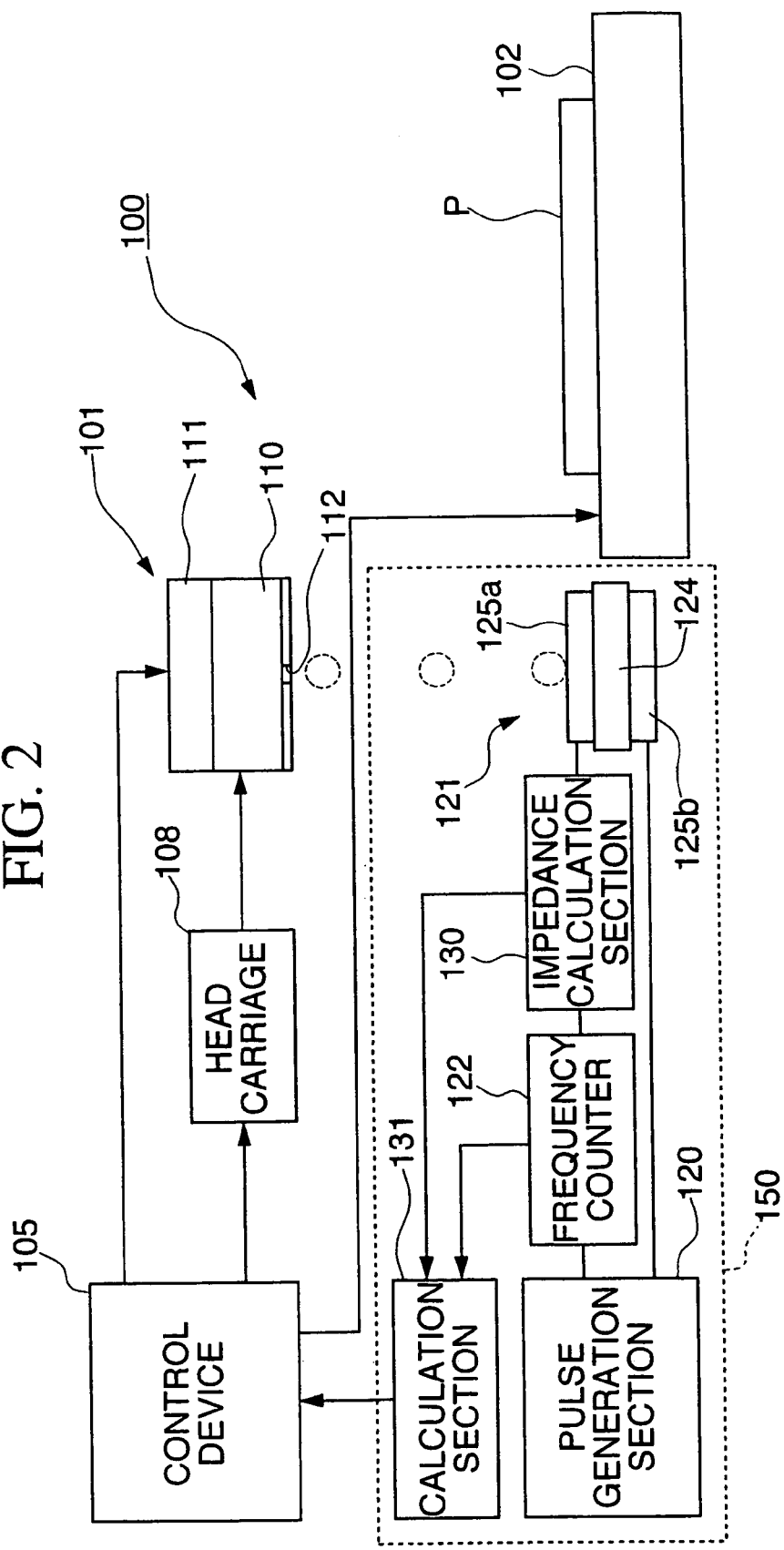
FIG. 2 is a figure showing schematically an example of the structure of a droplet discharge apparatus according to a first embodiment of the present invention.

Furthermore, the structure of the sensor tip 221 is the same as that of the sensor tip 121 shown in FIG. 2 according to the first embodiment.

Returning to FIG. 16, the sensor tip 221 is provided with an electrode 225a on its one side so as to oppose the droplet discharge surface upon the discharge head 201. When a droplet which has been discharged from the discharge head 201 adheres to the electrode 225a, the mass of this droplet which has adhered to the electrode 225a is calculated by the measuring apparatus 204. Furthermore, during this measurement, the head carriage 208 shifts the discharge head 201 so that the droplet adheres to the surface of the electrode 225a.

The quartz crystal oscillator 224 vibrates at a constant resonant frequency if the external force which acts upon it is constant, but it is endowed with the characteristic that, if an object adheres to the surface of the electrode 225a and the external force changes, its resonant frequency changes according to this amount of change of the external force. In other words, the quartz crystal oscillator 224 is endowed with the characteristic that, if an object adheres to the electrode 225, it vibrates at a resonant frequency which corresponds to the mass of that object. If the object which has adhered is endowed with viscoelasticity, the resonant frequency of the quartz crystal oscillator 224 changes according to the viscosity of that object. Furthermore, the measuring apparatus 204 of this example is one which is not endowed with any function of correcting errors due to the influence of viscoelasticity; in other words, it is a device of the so called self-excited type.

The frequency counter 222 detects the resonant frequency of the quartz crystal oscillator 224, and supplies an oscillation which indicates the result of this detection to the calculation section 223. Then, when the calculation section 223 inputs this signal which has been outputted from the frequency counter 222 which specifies the resonant frequency, it uses it to obtain the mass of the droplet.

Furthermore, the resonant frequency change of the quartz crystal oscillator 224 which is detected by the frequency counter 222 is the same as the change of frequency shown in FIG. 11. In addition, the continuation time period in the roughly steady state which is to be the standard for detection is determined appropriately according to the characteristics of the measuring apparatus 204 and the measurement accuracy which is required.

Here, the time difference <T1-T2> between the discharge time <T1> and the adhesion time <T2> is the flying time of the droplet from when the droplet is discharged from the discharge head 201 to when it collides with and adheres to the sensor tip 221. Accordingly, it is possible to calculate the speed of flying off of the droplet (its discharge speed) from the above described time difference and the distance from the discharge head 201 to the sensor tip 221 (the electrode 225a). In other words, if the above described distance is Lj, and the speed of flying off of the droplet is Vj, then Vj=Lj/|T1−T2|. This calculation is performed in the calculation section 223 (refer to FIG. 16).

In addition, since the frequency <fb> after drying is one which corresponds to the dried layer resulting from the droplet, it is possible to calculate the mass of the solid component of the droplet (the amount of its solid component) from the difference <fa−fb> between the frequency <fa> before adhesion of the droplet and the frequency <fb> after it has dried. In other words, it is possible to calculate the amount of the solid component of the droplet by substituting the above described amount of change of the frequency into a predetermined calculation equation which corresponds to the characteristic of the quartz crystal oscillator 224. Although the measuring apparatus 204 of this example is one which is not endowed with any function of correction for the influence of viscoelasticity, since no result of measurement during drying of the droplet is utilized in the above described calculation of the amount of the solid component, accordingly a stabilized measurement result is obtained while avoiding any influence upon the measurement due to viscoelasticity of the droplet.

In addition, the mass of the droplet which has adhered to the sensor tip 221 is calculated by the calculation section 223 from the above described result of calculation of the amount of the solid component, and from the concentration of the solid component in the droplet, in other words, from the initial solid component concentration of the liquid material which is supplied to the discharge head 201. In other words, when the solid component concentration of the liquid material is taken as c (%), the amount of the solid component which has been measured by the measuring apparatus 204 is taken as ms, and the mass of the droplet is taken as Im, then Im=(ms/c)×100. The mass Im of the droplet which is calculated here is one which does not include any influence due to viscoelasticity of the droplet, and has a stabilized accuracy. Furthermore, if no solid component is included in the liquid material which is utilized, or if although some solid component is included the amount thereof is extremely small, then it will be acceptable to add a solid component to the liquid material in advance, within the range in which the characteristics of the liquid material do not vary greatly. In addition, before measuring the above described droplet information, it is beneficial to discharge a preparatory droplet from the discharge head 201 at a place which is different from the sensor tip 201, in order to eliminate any difference in concentration between the liquid material which is supplied to the discharge head and the droplets which have actually been discharged (this is termed "flushing").

Now, when discharging a droplet from the discharge head 201, the target value for the amount of this droplet discharge (the amount of material in the droplet) is determined (for example at 10 ng (nanograms)), and a drive waveform which corresponds to this target value is supplied from the control device 205 to the discharge head 201. However, it may happen that the actual amount of material in the droplet is different from this target value, due to various errors such as change of the characteristics of the liquid material within the discharge head 201, errors in the response characteristic of the piezo element 211, errors in the volume of the pressure chamber 210, errors in the outer diameter of the nozzle 212, and the like. If the actual amount of material in the droplet is different from the target value, this invites deterioration of the accuracy of deposition of the liquid material upon the substrate P.

In addition, the above described error exerts an influence upon the speed of flying off of the droplet as well. If the actual speed of flying off of the droplet is different from the target value, then, during deposition of the droplet upon the substrate P while shifting the discharge head 201 and the substrate P with respect to one another, or the like, it may happen that its collision and adhesion position deviates from the target position.

With the droplet discharge apparatus of this example, the information for the droplet which is discharged from the discharge head 201 is measured by the measuring apparatus 204, and, based upon the result of this measurement, the drive waveform which is supplied to the discharge head 201 is set so as to bring the actual amount of material in the droplet and the actual speed of flying off of the droplet towards their target values. In other words, the control device 205 utilizes the current drive waveform (the standard drive waveform) if the measurement results of the measuring apparatus 204 fall within a certain standard. Conversely, if the above described measurement results fall outside the standard, by changing the drive waveform, it establishes discharge conditions (a drive waveform) which are most suitable. This optimization of the drive waveform may be performed by, for example, storing various types of droplet information in advance in correspondence with the most suitable drive waveforms for them, and by selecting from among this stored data the one which conforms to the measurement results of the measuring apparatus 204. Alternatively, the discharge of the droplet and the measurement of the droplet information may be repeated while varying the drive waveform so that the various items of droplet information are brought within the standard (feedback control). In this manner, with the droplet discharge apparatus 200 of this example, it is possible to perform the droplet discharge in a stabilized manner at high accuracy by striving to optimize the drive waveform for the discharge head 201 based upon the measurement results of the measuring apparatus 204.

Furthermore, as for other examples of the resonant frequency change of the quartz crystal oscillator 224 which is detected by the frequency counter 222 as well, they are the same as FIG. 12.

In addition, the drying process for the droplets in correspondence to change of frequency is the same as the drying process shown in FIG. 13A and FIG. 13B as well.

In this case, from the results of detection of frequency, it is possible to calculate the speed of flying off of the droplet, the amount of the solid component of the droplet, and the mass of the droplet, in the same way as in the previous FIG. 11. These measurement results are ones which do not include any influence of viscoelasticity of the droplet, and accordingly they have stabilized accuracy.

In addition, among the above described results of detection of frequency, it is possible to check the state of the drying process of the droplet from the change of frequency during the time period from the adhesion time <T6> to the time <T7> that the drying is completed (the time period <T6−T7>). In other words, by contrast to the change of frequency along with the lapse of time with the drying time period <T2−T3> shown in the previous FIG. 11, with the drying system shown in FIG. 12, the frequency attains a roughly steady state with respect to the lapse of time. Accordingly, it is possible to determine whether either of the phenomena of pinning and depinning is occurring by detecting the amount of change of the frequency during this drying time period (the tendency of the graph of the change of frequency). In more concrete terms, for example, it is possible to decide upon pinning if the amount of change of the frequency in a predetermined time period during the drying time period exceeds a standard value, and to decide upon depinning if it is less than or equal to the standard value.

With the droplet discharge apparatus 200 of this embodiment, among the droplet information which is measured by the measuring apparatus 204, the drying conditions for the droplet are controlled based upon the above described information related to the drying process of the droplet. In other words, the control device 205 checks whether or not the drying process of the droplet, as obtained from the results of measurement of the measuring apparatus 204, is in the state which is being aimed at; in concrete terms, which of pinning and depinning it is. Then, if it is different from the drying process which is being aimed at, the drying conditions for the droplet are controlled. This control of the drying conditions, for example, is performed via a drying device not shown in the figures, such as a blower, a lamp anneal, a hot plate, an electric over, or the like. In addition, it is also possible to control the drying conditions by varying the relative shifting speed of the droplet with respect to the atmosphere, as will be explained in the following.

Furthermore, with regard to the exemplary arrangement of the sensor tip 221 of the measuring apparatus 204, it may be the same as the example of arrangement shown in FIG. 4.

Here, during the measurement of the droplet information, when the droplet is deposited upon the sensor tip 221 (the electrode 225a), then the above described stage 202 shifts in the XY plane at a predetermined speed. When the stage 202 shifts, the drying of the droplet is promoted due to reduction of the vapor concentration of the vapor phase in the vicinity of the droplet and the like. The greater is the speed of shifting of the stage 202, the greater does the relative shifting speed of the droplet with respect to the atmosphere become, so that the greater does the drying speed of the droplet become. In addition, in the drying process of the droplet, the greater is the drying speed at the edge of the droplet as compared with the central portion of the droplet, the easier is it for pinning to occur; while, the smaller is the drying speed at the edge of the droplet, the easier is it for depinning to occur.

As a method of control of the drying conditions, for example, when it has been checked that the actual drying process is depinning, then the shifting speed of the stage 202 is made to be greater than at the present time point irrespective of whether or not the drying process of the droplet which is being aimed at is pinning. Conversely, when it has been checked that the actual drying process is pinning, then the shifting speed of the stage 202 is made to be less than at the present time point, irrespective of whether or not the drying process of the droplet which is being aimed at is depinning. By doing this, it becomes possible to control the dried layer of the droplet to the desired state.

In this manner, with the droplet discharge apparatus 200 of this embodiment, the drying conditions of the droplet are controlled based upon the droplet information which is measured by the measuring apparatus 204, and thereby the drying state of the droplet is controlled. As a result, it is possible to strive to optimize the drying conditions when depositing the liquid material upon the substrate P.

Furthermore, the sensor tip 221 and the substrate P which is to be processed are shifted together as one unit upon the same stage 202, and moreover the heights of their surfaces upon which the droplets adhere are roughly equal to one another. Due to this, the difference between the environmental conditions for the sensor tip 221 and the substrate P is small, so that there is the beneficial aspect that it is possible to utilize the measurement result using the sensor tip 221 effectively during the actual processing as well.

Figure 17:
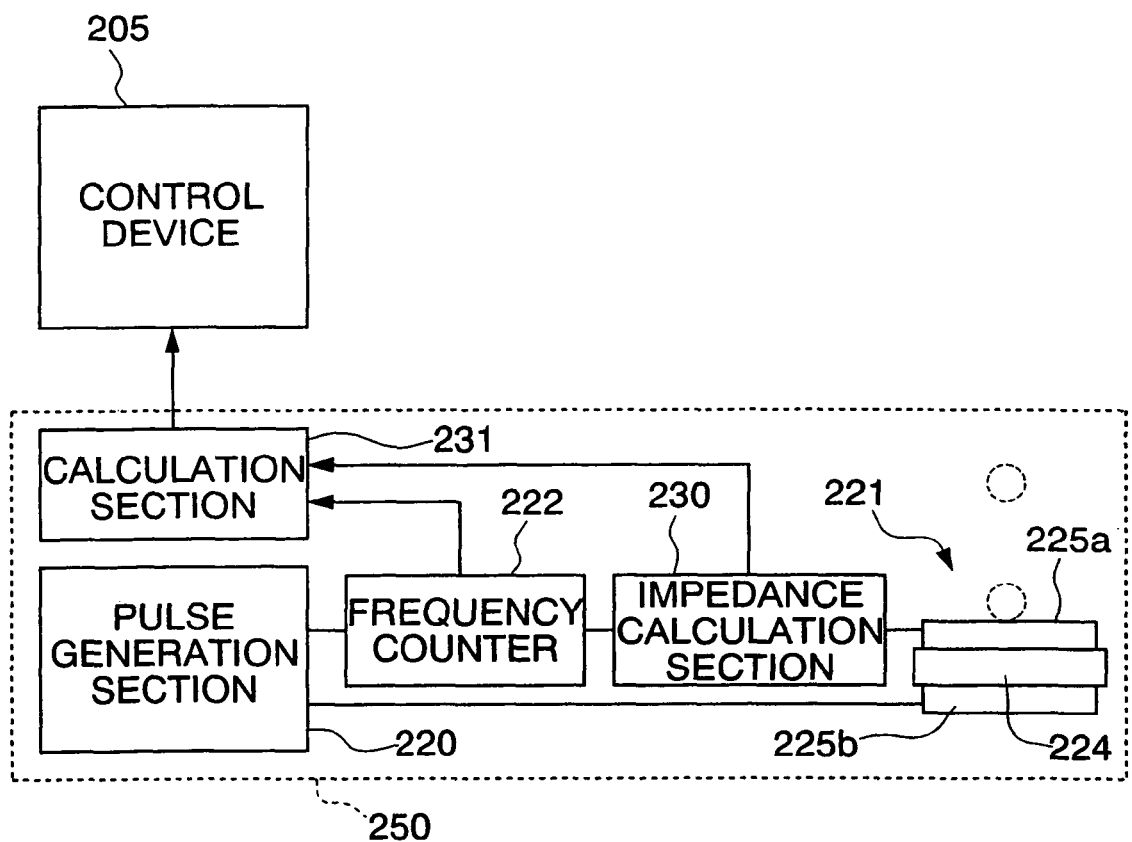
FIG. 17 is a figure showing another example of a droplet information measuring apparatus.

FIG. 17 is a figure showing another example of a droplet measuring apparatus (the measuring apparatus 250). Furthermore, with regard to the structural elements of the measuring apparatus, to ones which are endowed with the same functions as those of the measuring apparatus 204 previously shown in FIG. 16 the same reference symbols are appended, and their explanation will be curtailed or simplified.

The measuring apparatus 250 shown in FIG. 17 is different from the measuring apparatus 204 shown previously, in that it is possible to correct for the influence of the viscoelasticity of the object being measured, so that it is a so called external scan type device.

In FIG. 17, the measuring apparatus 250 includes a pulse generation section 220, a sensor tip 221, a frequency counter 222, an impedance calculation section 230, and a calculation section 231. The quartz crystal oscillator, as previously described, along with vibrating at a resonant frequency which corresponds to the mass of the droplet, also is endowed with the characteristic that its resonant frequency changes according to the viscosity of this object. The measuring apparatus 250 is one which takes advantage of this characteristic of the quartz crystal oscillator, and obtains the mass and the viscosity of the droplet. Furthermore it is possible to obtain the electrical impedance of the quartz crystal oscillator 224 with respect to frequency from the relationship between the electrical voltage which is applied to the quartz crystal oscillator 224 and the current. This impedance changes greatly in the vicinity of the resonant frequency. The frequency when the resistance component of the impedance becomes minimum is the resonant frequency, and this resistance component becomes the resonant resistance value.

The impedance calculation section 230 obtains the resonant resistance value of the quartz crystal oscillator 224 by calculation, and supplies a signal which indicates this resonant resistance value to the calculation section 231. In addition, the frequency counter 222 detects the resonant frequency of the quartz crystal oscillator 224, and supplies a signal which indicates the result of this detection to the calculation section 231. The calculation section 231 takes in this signal which indicates the resonant resistance value which has been outputted from the impedance calculation section 230, and this signal which indicates the resonant frequency which has been outputted from the frequency counter 222, and calculates the viscosity and the mass of the droplet by utilizing them. In this case, the calculation is made using Equations 1 to 3, in the same manner as explained for the impedance calculation section 130 of the first embodiment.

Furthermore, with the measuring apparatus 250 of this embodiment, by considering the viscoelasticity of the droplet, in addition to the solid component of the droplet, the mass of the liquid component of the droplet may also be detected. Due to this, during the drying of the droplet, the frequency changes according to the change of mass of the droplet due to the evaporation of its liquid component (the solvent, the dispersion medium, or the like). In addition since, after the droplet has dried, all the liquid component has evaporated and the mass does not change, thus the frequency attains a roughly steady state with respect to the lapse of time. Accordingly, after discharge of the droplet, it is possible to obtain the time <T13> at which this droplet has completely dried by detecting the starting time point of the frequency being in a roughly steady state continuously for more than a predetermined time period.

In addition, from the detection result for the above described frequency, it is possible to calculate the speed of flying off of the droplet and the amount of the solid component of the droplet, in the same manner as in the case of the previous FIG. 11.

In other words, if the distance from the discharge head 201 to the sensor tip 221 (the electrode 225a) is taken as Lj, and the speed of flying off of the droplet is taken as Vj, then Vj=Lj/|T11−T12|.

In addition, since the frequency <fb> after drying is one which corresponds to the dried layer of the droplet, it is possible to calculate the mass of the solid component of the droplet (the solid component amount) from the difference <fa−fb> between the frequency <fa> before adhesion of the droplet and the frequency <fb> after it has dried.

In addition, it is possible to calculate the mass of the droplet (its discharge amount) from the difference <fa−fc> between, among the above described results of detection of frequency, the frequency <fa> before adhesion of the droplet, and the frequency <fc> when the droplet has adhered. In other words, it is possible to obtain the mass of the droplet by substituting the difference <fa−fc> of the above described frequencies as the amount of change of frequency Δfreq in the Equations. In addition, in the same manner, it is possible to calculate the mass of the droplet at a predetermined time point during drying from the difference <fa−fd> between the frequency <fa> before adhesion of the droplet and the frequency <fd> at a predetermined time point (for example, at the time <Ta>).

In this manner, it is possible to calculate the actual amount of a droplet which has been discharged from the discharge head 201, the actual speed of flying off of this droplet, and the like with the measuring apparatus 250 of this embodiment as well. Accordingly, it is possible to promote optimization of the drive waveform which is supplied to the discharge head 201 which was shown in the previous FIG. 16 by using this measuring apparatus 250.

Figure 18A:
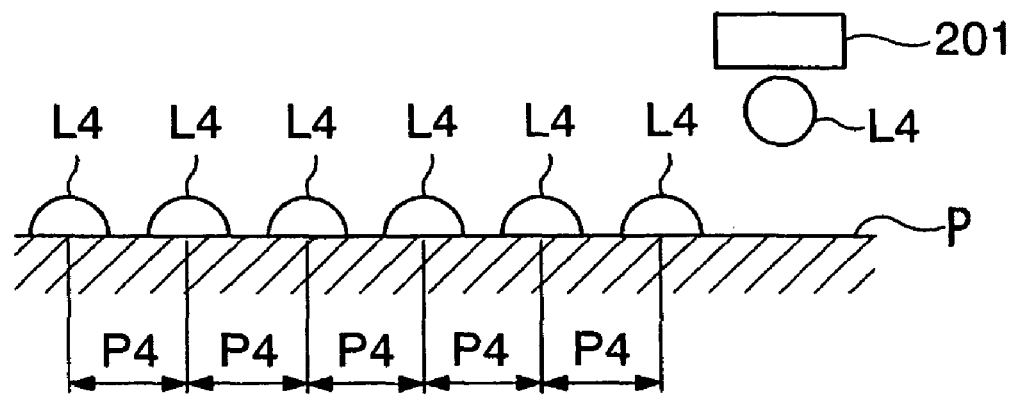
FIGS. 18A to 18C are figures showing an example of procedures of a method for forming a linear film pattern upon a substrate.
Figure 18B:
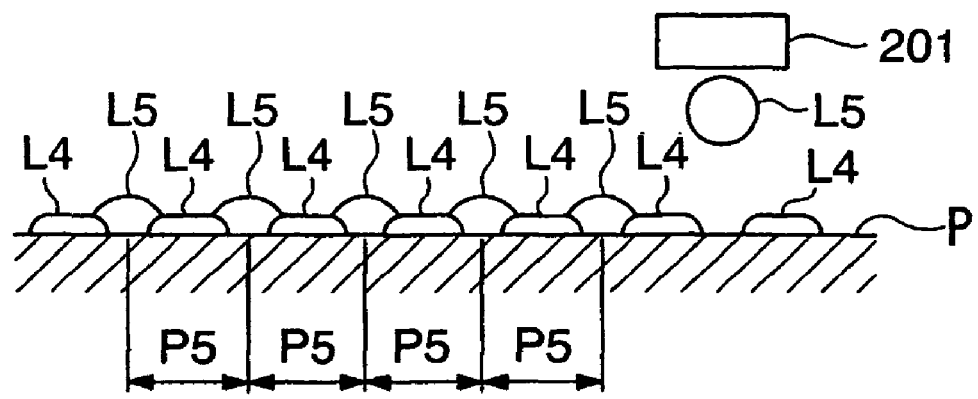
Figure 18C:

FIGS. 18A to 18C show an example of procedures of a method for forming a linear film pattern upon a substrate, using the above described droplet discharge apparatus 200.

With this film pattern forming method, the liquid material is discharged from the discharge head 201 as droplets, and these droplets are deposited upon the substrate P at a fixed distance apart from one another (pitch). Then, a linear film pattern is formed upon the substrate P by repeating this deposition action of the droplets.

In concrete terms, first, as shown in FIG. 18A, droplets L4 which have been discharged from the discharge head 201 are deposited in order upon the substrate P with a fixed interval being left between them. In this example, the deposition pitch P4 of the droplets L4 is determined so as to be greater than the diameter (the radius upon collision and adhesion) of the droplets L4 directly after they have been deposited upon the substrate P. Due to this, the droplets L4 do not mutually contact one another directly after they have been deposited upon the substrate P, so that spreading out upon the substrate P of the droplets L4 by mutual combination together is prevented.

After the droplets L4 have been deposited upon the substrate P, according to requirements, a drying procedure is performed in order to perform elimination of their liquid component (solvent or dispersion medium). With regard to this drying procedure, apart from employing a conventional type of heating procedure using a heating device such as, for example, a hot plate, an electric oven, a hot air blower, a lamp anneal or the like, it may be performed by shifting the stage upon which the substrate P is carried.

Next, as shown in FIG. 18B, the above described action of deposition of the droplets is repeated. In other words, in the same manner as for the previous episode shown in FIG. 18A, liquid material is discharged from the discharge head 201 as droplets L5, and these droplets L5 are deposited upon the substrate P at a fixed distance apart. At this time, the amount of material in the droplets L5 (the amount of liquid material in a single droplet) and their deposition pitch P5 are the same as for the droplets L4 of the previous deposition episode. In addition, the positions of deposition of the droplets L5 are shifted by just ½ of the pitch from the droplets L4 of the previous episode, so that the droplets L5 for this episode are deposited in intermediate positions between the individual droplets L4 of the previous episode which are deposited upon the substrate P. By thus depositing the droplets L5 in intermediate positions between the droplets L4, the droplets L5 become unified with the droplets L4, so that the gaps between the individual ones of the droplets L4 are filled up.

In addition, at this time, although the droplets L5 of this episode are in contact with the droplets L4 of the previous episode, since the liquid component in the droplets L4 of the previous episode has already completely or at least to some extent been eliminated, accordingly the two of them do not much combine together and spread out upon the substrate P. After the droplets L5 have been deposited upon the substrate P, in order to perform elimination of the liquid component therein, in the same way as in the previous episode, according to requirements, a drying procedure is performed.

By repeating the action of depositing a series of droplets in this manner a plurality of times, the gaps between the individual droplets which are deposited upon the substrate P are filled in, and, as shown in FIG. 18C, a continuous linear pattern is formed upon the substrate P. In this case, by increasing the number of repetitions of the action of deposition of droplets, the droplets become laid up in series upon the substrate P, and the layer thickness of the linear pattern, in other words the height (the thickness) from the surface of the substrate P is increased. The height (the thickness) of the linear pattern is determined according the desired layer thickness which is considered to be necessary for the final film pattern, and the number of times for repetition of the action of deposition of the above described droplets is determined according thereto.

When forming the above described film pattern, before depositing the liquid material from the discharge head 201 upon the substrate P, or during the deposition of the liquid material, information about the droplets which are being discharged from the discharge head 201 is measured by the measuring apparatus 204 (refer to FIG. 16), and, based upon the results of this measurement, the drive waveform which is supplied to the discharge head 201 is set so that the actual amount of material in the droplet, and the actual speed of flying off of the droplet approach towards their target values. In addition, before depositing the liquid material, the drying conditions for the droplet are also optimized. By doing this, with the film pattern forming method of this example, along with depositing droplets of the target masses exactly in the target positions upon the substrate P, also the desired dried layer is formed. Due to this, it is possible to form a film pattern at high accuracy in a stabilized manner.

Furthermore, this method of forming a linear pattern is not limited to the one which is shown in FIGS. 18A to 18C. For example, it is possible to set the deposition pitch of the droplets, and the shift amount during repetition, and the like, as desired.

Furthermore, the droplet discharge apparatus of this embodiment is suitable for the manufacture of a liquid crystal display apparatus which is fitted with a color filter of the type shown in FIG. 14.

In addition, it is a matter of course that it is possible to apply the above described liquid crystal display apparatus to an electronic apparatus such as the one shown in FIG. 15.

Third Embodiment

The basic structure of the droplet discharge apparatus which is used in this embodiment is the same as the droplet discharge apparatus shown in FIG. 2. In the following explanation, to elements which are the same as structural elements which are shown in FIG. 2, the same reference symbols are appended, and explanation of the same contents as in the above described embodiment will be curtailed.

Here, the time difference <T11−T12> between the discharge time <T11> in FIG. 5 and the adhesion time <T12> is the flying time of the droplet from when the droplet is discharged from the discharge head to when it collides and adheres to the sensor tip 121. Accordingly, it is possible to calculate the speed of flying off of the droplet (its discharge speed) from the above described time difference and the distance from the discharge head 101 to the sensor tip 121 (the electrode 125a). In other words, if the above described distance is taken as being Lj, and the speed of flying off of the droplet is taken as being Vj, then Vj=Lj/|T11−T12|. This calculation is performed by the calculation section 131 (refer to FIG. 2).

In addition, since the frequency <fb> after drying is one which corresponds to the dried layer of the droplet, accordingly it is possible to calculate the mass of the solid component of the droplet (the solid component amount) from the difference <fa−fb> between the frequency <fa> before adhesion of the droplet and the frequency <fb> after it has dried.

In addition, it is possible to calculate the mass of the droplet (its discharge amount) from the difference <fa−fc> between, among the above described results of detection of frequency, the frequency <fa> before adhesion of the droplet, and the frequency <fc> when the droplet adheres. In other words, if the above described difference of frequency <fa−fc> is taken as being the amount of change of frequency Δfreq, it is possible to obtain the mass of the droplet by substituting it in said Equations. In addition, in the same manner, it is possible to calculate the mass of the droplet at a predetermined time point during its drying from the difference <fa−fd> between the frequency <fa> before adhesion of the droplet, and the frequency <fd> at the predetermined time point (for example, at the time <Ta>).

In addition, the solid component concentration of the droplet which has adhered to the sensor tip 121 is calculated from the calculation result of the solid component amount and the calculation result of the mass of the droplet which have been described above.

In other words, when the mass of the droplet which has been measured by the measuring apparatus 150 is taken as being lm, the solid component amount which is measured by the measuring apparatus 150 is taken as being ms, and the solid component concentration of the droplet is taken as being c, then c=lm/ms.

By the way, the diameter of the nozzle 112 (refer to FIG. 2) which is used in the discharge head 101 for droplet discharge is extremely small, and, if drying of the liquid material proceeds within the nozzle 112, it is easy for blocking thereof to occur. In other words, by the solid component concentration of the liquid material within the nozzle 112 mounting, there is a possibility of the solid component which is included in the liquid material solidifying or condensing within the nozzle 112, and of the nozzle 112 being thereby closed off.

In this embodiment, a decision is made as to the drying state of the nozzle 112 based upon the droplet information which is obtained from the measuring apparatus 150, and blocking of the nozzle 112 is prevented in advance.

In the following, an example of processing for preventing blocking of the nozzle 112 in advance will be explained with reference to the flow chart of FIG. 19.

As described above, the measuring apparatus 150 measures (in a step 101) the droplet information of the droplet which has been discharged from the discharge head 101. The control device 105 compares together (in a step 102), among the measurement results of the measuring apparatus 150, the solid component concentration of the droplet, and the initial solid component concentration of the liquid material which is supplied to the discharge head 101. Then, (in a step 103) a decision is made as to what extent the liquid material within the nozzle 112 has dried.

In concrete terms, the initial solid component concentration of the liquid material is inputted in advance into the control device 105, and the control device 105 makes a decision as to whether or not the proportion of this solid component concentration of the droplet with respect to the initial solid component concentration is greater than a standard value. For example, if the above described proportion exceeds the standard value (for example 120%), then it is decided that the drying state of the nozzle 112 is progressing, while if it is less than the standard value, then it is decided that the drying state of the nozzle 112 is not progressing. Then, if it is decided that the drying state of the nozzle 112 is progressing, then the control device 105 controls the drive conditions of the discharge head 101 (in a step 104), and aims to prevent blocking of the nozzle 112 in advance.

Prevention of blocking in advance, for example, is performed by stirring the liquid material within the nozzle 112 (meniscus shaking), or by performing preliminary droplet discharge from the nozzle 112 upon a place which is different from the sensor tip 121 (preliminary discharge, or flushing). Or it may be performed by varying the conditions for implementing the above described meniscus shaking or the above described preliminary discharge.

Here, FIG. 20 shows an example of a drive signal which is supplied to a piezo element.

In FIG. 20, the drive waveform <A> is the basic waveform which is created by the drive signal generation circuit. <Part 1> of this waveform is used for diffusing the liquid in the vicinity of the nozzle opening whose viscosity has increased by shaking the meniscus (the concave and convex surface of the liquid within the nozzle), and for thus preventing poor discharge of the minute droplets in advance of its happening. Then, <B1> is the state in which the meniscus is smooth and stable, while <B2> shows an action for expanding the volume of the pressure chamber (of the liquid chamber) by gently supplying electricity to the piezo element, thus pulling the meniscus a little into the nozzle.

In the step 104 of FIG. 19, the control device 105, for example, supplies the drive waveform described above for shaking the meniscus to the discharge head 101. In addition, if a drive waveform for shaking the meniscus is already being supplied to the discharge head 101, it increases the amplitude of this drive waveform, and/or shortens its period. By doing this, stirring of the liquid material within the nozzle 112 is promoted, so that it is possible to prevent blocking of the nozzle 112 in advance.

In addition if, in the step 103 of FIG. 19, it is decided that the drying of the nozzle 112 is not progressing, then the control device 105 establishes a correspondence between the solid component concentration of the droplet which has been measured by the measuring apparatus 150, and the time which has elapsed from the time of discharging the previous droplet, and temporarily stores this in an internal memory (in a step 105). By accumulating this data, it becomes possible to grasp the state of affairs with regard to the changes of concentration of the liquid material within the nozzle 112 with respect to lapse of time; for example, to obtain the time period from the discharge of a droplet until the nozzle 112 dries. As a result, it becomes possible to obtain the time period over which it is possible to leave the nozzle 112 (the discharge head 101) alone (the permissible waiting time), and the most suitable timing for performing nozzle blocking prevention processing in advance (meniscus shaking or preliminary discharge or the like).

In this manner, with the droplet discharge apparatus 100 of this example, it is possible to detect the drying state of the nozzle 112 at a state before blocking of the nozzle 112 has actually occurred, and, because blocking of the nozzle 112 is prevented in advance based upon the result of this detection, it becomes possible to prevent deterioration of the productivity which accompanies blocking of the nozzle 112. Furthermore, since increase of the concentration of the liquid material within the nozzle 112 is a cause of error in the discharge amount of material in the droplets and in the speed of flying off of the droplets, accordingly it would also be acceptable to control the drive conditions of the discharge head 101 so as to keep the solid component concentration of the droplets which is measured by the measuring apparatus 150 to be always roughly constant. By doing this, in addition to preventing blocking in advance, it also becomes possible to perform the droplet discharge in a stabilized manner at high accuracy.

Furthermore the droplet discharge apparatus of this embodiment can appropriately manufacture a liquid crystal display apparatus which is equipped with a color filter such as that shown in FIG. 14.

In addition, it is a matter of course that it is possible to apply the above described liquid crystal display apparatus to an electronic apparatus such as the one which is shown in FIG. 15.

Furthermore, the application of the droplet discharge apparatus is not limited to patterning of a color filter which is used in an electro-optical apparatus, as in the above described embodiment; it is possible to use it in the manufacture of various types of film pattern, as in the following. For example, it can be utilized in the formation of a thin film for an organic EL layer or a positive hole injection layer or the like which is included in an organic EL (electroluminescence) display panel. If it is used in the manufacture of such an organic EL layer, then droplets which include an organic EL material such as, for example, a polythiophen type electrically conductive high molecular weight material or the like, are discharged against regions which are delimited by division walls which are formed upon a substrate, so that the droplets are deposited in these regions. Then, an organic EL layer is formed by drying the liquid material which has been deposited in this manner.

In addition, as other applications of this droplet discharge apparatus, there is the manufacture of auxiliary wiring for a transparent electrode which is included in a plasma display, or of a device such as an antenna or the like which is included in an IC (an integrated circuit) card or the like. In concrete terms, after, using this droplet discharge apparatus, patterning with a solution which is a mixture of minute electrically conductive particles such as minute particles of silver or the like in an organic solution such as tetradecane or the like, the thin metallic layer is formed when the organic solution is dried.

Moreover, apart from the cases described above, this droplet discharge apparatus may also be utilized, for example, for depositing various types of material such as, apart from a thermosetting resin which is used in manufacturing solid objects, or an ultraviolet setting resin or the like, also a micro lens array material or a bio-material such as DNA (deoxyribonucleic acid) or a protein or the like.

In addition, as an electronic apparatus, apart from a portable telephone, there may be suggested a computer, or a projector, a digital camera, a movie camera, a PDA (Personal Digital Assistant), a vehicle mounted device, a copy machine, an audio device, or the like.

While preferred embodiments of the invention have been described and illustrated above, furthermore these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A droplet discharge apparatus comprising:
a discharge head that discharges a droplet;
a droplet information measuring apparatus that measures information of the discharged droplet; and
a control device that controls the discharge head, wherein:
the droplet information measuring apparatus includes:
an oscillator that has a surface receiving the discharged droplet;
a detection section that detects a frequency of the oscillator; and
a calculation section that calculates a mass of the discharged droplet,
the control device controls the discharge head based on a first frequency and a second frequency, the first frequency being a first oscillating frequency of the oscillator when the surface does not receive the discharged droplet, and the second frequency being a second oscillating frequency of the oscillator when the discharged droplet has dried on the surface,
the discharged droplet includes a solid component and a liquid component, and the solid component in the discharged droplet remains on the surface when the discharged droplet has dried on the surface,
the calculation section calculates a mass of the solid component in the discharged droplet and further calculates a concentration of the solid component in the discharged droplet,
liquid material is provided to the discharge head as a source of the discharged droplet,
an initial concentration of the solid component of the liquid material is input to the control device,
the control device compares the solid component in the discharged droplet and a standard value of the solid component of the liquid material,
the standard value is based on the initial concentration of the solid component of the liquid material, and
the control device controls the discharge head based on the comparison result so as to prevent blocking of a nozzle.

2. The droplet discharge apparatus according to claim 1, wherein
the surface is a surface of an electrode.

* * * * *